(12) United States Patent
Corey et al.

(10) Patent No.: US 11,795,457 B2
(45) Date of Patent: Oct. 24, 2023

(54) COMPOSITIONS AND METHODS FOR TREATMENT OF FRIEDREICH'S ATAXIA

(71) Applicant: The Board of Regents of The University of Texas System, Austin, TX (US)

(72) Inventors: David Corey, Dallas, TX (US); Liande Li, Dallas, TX (US)

(73) Assignee: The Board of Regents of The University of Texas System, Austin, TX (US)

(*) Notice: Subject to any disclaimer, the term of this patent is extended or adjusted under 35 U.S.C. 154(b) by 0 days.

(21) Appl. No.: 17/486,136

(22) Filed: Sep. 27, 2021

(65) Prior Publication Data

US 2022/0017903 A1  Jan. 20, 2022

Related U.S. Application Data

(63) Continuation of application No. 15/534,761, filed as application No. PCT/US2015/064439 on Dec. 8, 2015, now abandoned.

(60) Provisional application No. 62/126,977, filed on Mar. 2, 2015, provisional application No. 62/089,678, filed on Dec. 9, 2014.

(51) Int. Cl.
| | |
|---|---|
| *C07H 21/04* | (2006.01) |
| *C12N 15/113* | (2010.01) |
| *A61P 25/00* | (2006.01) |
| *A61K 45/06* | (2006.01) |

(52) U.S. Cl.
CPC ............ *C12N 15/113* (2013.01); *A61K 45/06* (2013.01); *A61P 25/00* (2018.01); *C12N 2310/14* (2013.01); *C12N 2310/315* (2013.01); *C12N 2310/3231* (2013.01)

(58) Field of Classification Search
None
See application file for complete search history.

(56) References Cited

U.S. PATENT DOCUMENTS

| | | | |
|---|---|---|---|
| 7,056,704 B2 * | 6/2006 | Tuschl | A61P 31/12 435/6.16 |
| 9,976,138 B2 | 5/2018 | Prakash et al. | |
| 2013/0239236 A1 | 9/2013 | Verhaert et al. | |
| 2014/0303238 A1 * | 10/2014 | Linsley | C07F 9/65616 536/24.5 |
| 2014/0316121 A1 | 10/2014 | Prakash et al. | |
| 2016/0178610 A1 * | 6/2016 | Buehler | A61K 31/444 435/367 |

OTHER PUBLICATIONS

Sandi et al. (Genetics Research International vol. 2013, Article ID 852,080, 12 pages).*

Evans-Galea et al., "Beyond loss of frataxin: the complex molecular pathology of Friedreich ataxia," *Discov. Med.*, 17(91):25-35, 2014.

Evans-Galea et al., "Cell and gene therapy for Friedreich ataxia: progress to date," *Hum. Gene Ther.*, 25(8):684-693, 2014.

Evans-Galea et al., "FXN methylation predicts expression and clinical outcome in Friedreich ataxia," *Ann. Neurol.*, 71(4):487-497, 2012.

Gottesfeld et al., "Increasing Frataxin Gene Expression with Histone Deacetylase Inhibitors as a Therapeutic Approach for Friedreich's Ataxia," *J. Neurochem.*, 126:147-154, 2013.

Janowski et al., "Activating gene expression in mammalian cells with promoter-targeted duplex RNAs," *Nat. Chem. Biol.*, 3(3):166-173, 2007.

Lima et al., "Single-stranded siRNAs inactivate the RNAi in Animals," *Cell*, 150: 883-894, 2012.

Marmolino, "Friedreich's ataxia: past, present and future," *Brain Res. Rev.*, 67: 311-330, 2011.

Matsui et al., "Activation of LDL receptor expression by small RNAs complementary to a noncoding transcript that overlaps the LDLR promoter," *Chem. Biol.*, 17: 1344-1355, 2010.

Matsui et al., "Promoter RNA links transcriptional regulation of inflammatory pathway genes," *Nucleic Acids Res.*, 41(22):10086-10109, 2013.

Office Action issued in U.S. Appl. No. 15/534,761, dated Aug. 25, 2020.

Office Action issued in U.S. Appl. No. 15/534,761, dated Apr. 19, 2019.

Office Action issued in U.S. Appl. No. 15/534,761, dated Dec. 20, 2019.

Office Action issued in U.S. Appl. No. 15/534,761, dated Jan. 23, 2019.

PCT International Preliminary Report on Patentability issued in corresponding PCT Application No. PCT/US2015/064439, dated Jun. 22, 2017.

PCT International Search Report and Written Opinion issued in corresponding PCT Application No. PCT/US2015/064439, dated Mar. 21, 2016.

Richardson et al., "Therapeutic strategies in Friedreich's ataxia," *Brain Res.*, 1514:91-97, 2013.

Sandi et al., "Epigenetics in Friedreich's Ataxia: Challenges and Opportunities for Therapy," *Genetics Research International*, (852080):1-12, 2013.

Schwartz et al., "Antisense transcripts are targets for activating small RNAs," *Nat. Struct. Mol. Biol.*, 15, 842-848, 2008.

Yu et al., "Single-stranded RNAs use RNAi to potently and allele-selectively inhibit mutant huntingtin expression," *Cell*, 150: 895-908, 2012.

Yue et al., "Regulation of transcription by small RNAs complementary to sequences downstream from the 30 termini of genes," *Nat. Chem. Biol.* 6:621-629, 2010.

Villasenor et al., "Genome-engineering tools to establish accurate reporter cell lines that enable identification of therapeutic strategies to treat Friedreich's ataxia," *Journal of Biomolecular Screening*, 20(6):760-767, 2015.

* cited by examiner

*Primary Examiner* — Kimberly Chong
(74) *Attorney, Agent, or Firm* — Parker Highlander PLLC

(57) ABSTRACT

Described are compounds and methods useful for the treatment and investigation of Friedreich's Ataxia.

14 Claims, 16 Drawing Sheets
Specification includes a Sequence Listing.

```
       UCUUCUUCUUCUUCUUCUU              SEQ ID NO: 50
       UUCUUCUUCUUCUUCUUCU              SEQ ID NO: 51
       CUUCUUCUUCUUCUUCUUC              SEQ ID NO: 52
---GAAGAAGAAGAAGAAGAAGAAGAAGAAGAA---    SEQ ID NO: 53
```
FIG. 1C
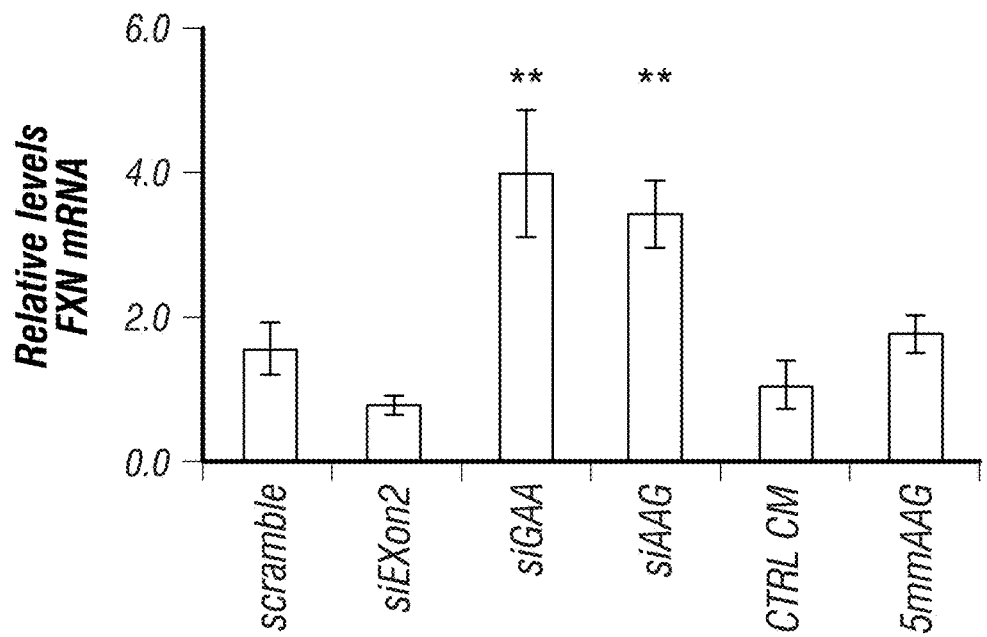
FIG. 1D
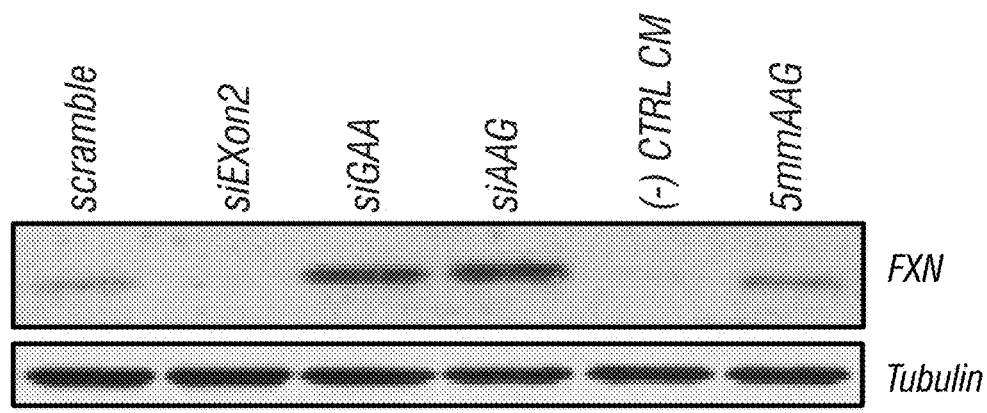
FIG. 1E
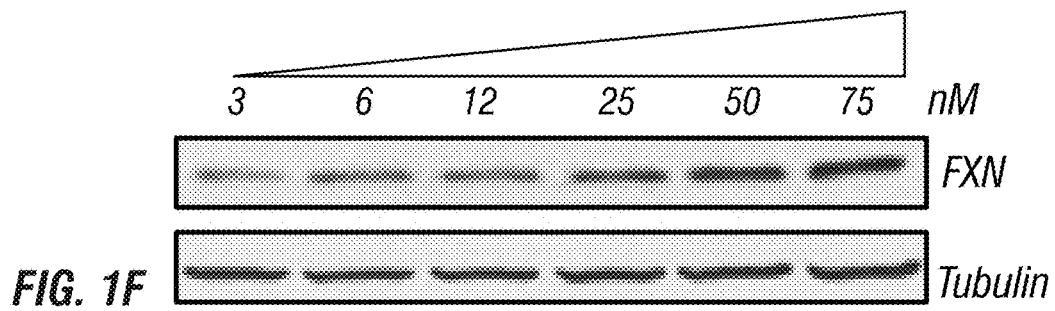
FIG. 1F

Locked nucleic acid (LNA)

*Ago2 RIPed sequence*

TATGCATTAATGGGTTATAATTCACTGAAAAATAGTAACGTACTTCTTAACTTTGGCTTTCAGA
GTTCGAACCAACGTGGCCCTCAACCAGATTTGGAATGTCAAAAAGCAGAGTGTCTATTTGATGAAA
TTTGAGGAAATCTGGAACTTTGGGC    SEQ ID NO: 54

*Sequenced Ago2 IP sequence*

>Ago2 IP sequence
NNNNNNNNNNNANNNNNNNNTATGCATTAATGGGTTATAATTCACTGAAAAATAGTAACGTACTTCTTAACTTTGGCTT
TCAGAGTTCGAACCAACGTGGCCTCAACCAGATTTGGAATGTCAAAAAGCAGAGTGTCTATTTGATGAATTTGAGGAAAT
CTGGAACTTTGGGNNNGANNTTCTNNNGTCCGGGCGNCNNNTCTCNCNCCNGNCTCNCTNGCATNCNTGGAGACCCAGT
CNCCNTCCCGTNCTGNNNCGNNGCATNANGANTNGGCNCNNNTNNTTTTNAGCCGAANNCNGNNTNTCACCNGNNC
NNGCCNGCANNNCNTTGCNTCTTNTNTGTNCAGCNGTNN

```
Query   22   TATGCATTAATGGGTTATAATTCACTGAAAAATAGTAACGTACTTCTTAACTTTGGCTTT    81
             ||||||||||||||||||||||||||||||||||||||||||||||||||||||||||||
Sbjct 69046322 TATGCATTAATGGGTTATAATTCACTGAAAAATAGTAACGTACTTCTTAACTTTGGCTTT  69046381

Query   82   CAGAGTTCGAACCAACGTGGCCTCAACCAGATTTGGAATGTCAAAAAGCAGAGTGTCTAT   141
             ||||||||||||||||||||||||||||||||||||||||||||||||||||||||||||
Sbjct 69046382 CAGAGTTCGAACCAACGTGGCCTCAACCAGATTTGGAATGTCAAAAAGCAGAGTGTCTAT  69046441

Query  142   TTGATGAATTTGAGGAAATCTGGAACTTTGGGC   174
             |||||||||||||||||||||||||||||||||
Sbjct 69046442 TTGATGAATTTGAGGAAATCTGGAACTTTGGGC  69046474    FXN gene locus
```

*Sequenced Ago2 IP sequence*

FIG. 11

COMPOSITIONS AND METHODS FOR TREATMENT OF FRIEDREICH'S ATAXIA

This application is a continuation of U.S. application Ser. No. 15/534,761, filed Jun. 9, 2017, which is a national phase application under 35 U.S.C. § 371 of International Application No. PCT/US2015/064439, filed Dec. 8, 2015, which claims benefit of priority to U.S. Provisional Application Ser. No. 62/089,678, filed Dec. 9, 2014, and U.S. Provisional Application Ser. No. 62/126,977, filed Mar. 2, 2015, the entire contents of each of which being hereby incorporated by reference.

This invention was made with government support under National Institute of General Medical Science GM073042-11 and GM106151-02 awarded by the National Institutes of Health. The government has certain rights in the invention.

BACKGROUND

1. Fields

The disclosure relates to the fields of genetics, medicine and molecular biology. In particular, the disclosure relates to nucleic acid compositions and their use in treating Friedreich's Ataxia.

2. Related Art

Friedreich's Ataxia (FRDA) is an incurable genetic disorder caused by reduced expression of the mitochondrial protein frataxin (FXN) (Pandolfo 2009; Collins 2013). FRDA patients have an expanded GAA repeat region within the first intron of the FXN-1 gene. This expanded repeat causes transcriptional silencing by a mechanism that has yet to be definitively described. Unlike neurological disease like Huntington Disease or Machado Joseph Disease, which are caused by the expression of mutant protein, patients with FRDA express normal FXN protein. If FXN protein could be increased towards normal levels, the progression of the disease would likely be slowed.

Agents that increase expression of FXN protein would correct the disease-causing defect and are a promising approach to therapy (Marmolino, 2011; Sandhi et al., 2013; Richardson et al., 2013; Gottesfeld et al., 2013). Reduced expression of FXN mRNA and protein is associated with changes in chromatin modification including increased H3K9 methylation and decreased H3K9 acetylation (Greene, et al., 2007; Al-Mahdawi et al., 2008; Kumari et al., 2012). Potential approaches for increasing FXN expression include the use of histone deacetylase inhibitors to reverse the epigenetic changes that contribute to decreased expression (Sandi et al., 2011; Gottesfeld et al, 2013, Chan et al., 2013; Libri et al., 2014; Soragni et al., 2014). Most recently, a screen of existing drugs identified the topical anesthetic Dyclonine as an activator of FXN expression, possibly by inducing expression of the transcription factor Nrf2 (Sahdeo et al., 2014).

These existing approaches are important directions for therapeutic development. However, the strategies rely on non-specific gene activation, a potential disadvantage that may disrupt progress in the clinic. A goal is to develop alternative strategies that use synthetic nucleic acids to sequence-specifically recognize expanded GAA mRNA, thereby avoiding the non-specific effects.

SUMMARY

Thus, the present disclosure provides a double-stranded oligonucleotide of 13 to 22 nucleobases in length and having a repeating tri-nucleobase sequence comprising (i) GAA or CUU or (ii) AAG or UUC. The oligonucleotide may comprise one or more chemically-modified nucleobases, such as a nuclease-resistant modification, such as a modified sugar moiety or a modified internucleoside linkage. The modified sugar moiety may be a high-affinity sugar modification, such as a bicyclic sugar moiety or a 2'-modified sugar moiety. The modified sugar moiety may be a 4' to 2' bicyclic sugar moiety, such as a 4'-CH$_2$—O-2' or 4'-CH(CH$_3$)—O-2' bicyclic sugar moiety, and more particularly where each 4' to 2' bridge independently may comprise from 2 to 4 linked groups independently selected from —[C(R$_a$)(R$_b$)]$_y$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_1$)—; wherein x is 0, 1, or 2; y is 1, 2, 3, or 4; each R$_a$ and R$_b$ is, independently, H, a protecting group, hydroxyl, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_5$-C$_9$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_5$-C$_{20}$ aryl, substituted C$_5$-C$_9$ aryl, acyl (C(=O)—H), substituted acyl, a heterocycle radical, a substituted heterocycle radical, C$_1$-C$_6$ aminoalkyl, substituted C$_1$-C$_6$ aminoalkyl or a protecting group. Even more particularly, each 4' to 2' bridge may independently be —[C(R$_c$)(R$_d$)]$_n$—, —[C(R$_c$)(R$_d$)]$_n$—O—, —C(R$_c$R$_d$)—N(R$_e$)—O— or —C(R$_e$R$_d$)—O—N(R$_e$)—, wherein each R$_c$ and R$_d$ is independently hydrogen, halogen, substituted or unsubstituted C$_1$-C$_6$ alkyl; and each R$_e$ is independently hydrogen or substituted or unsubstituted C$_1$-C$_6$ alkyl, and even more specifically, where each 4' to 2' bridge is independently a 4'-(CH$_2$)$_2$-2', 4'-(CH$_2$)$_{3-2',4}$'-CH$_2$—O-2',4'-CH(CH$_3$)—O—2',4'-(CH$_2$)$_2$—O-2', 4'-CH$_2$—O—N(R$_e$)-2' and 4'-CH$_2$—N(R$_e$)—O-2'-bridge.

The double-stranded oligonucleotide may comprise terminal dT residues. The double-stranded oligonucleotide may comprise 3' and/or '5 2'-O-methyl modifications. The double-stranded oligonucleotide may comprise (a) a central mismatch (within bases 9-14) with a target sequence comprising said repeating tri-nucleobase sequence, or (b) a mismatch outside of the seed sequence (bases 2-8 within the guide strand complementary to the GAA target sequence). The double-stranded oligonucleotide may comprise 4, 5, 6 or 7 repeats.

The nucleosides of the double-stranded oligonucleotide may be linked by phosphate internucleoside linkages, such as a phosphorothioate linkage, including where each internucleoside linkage is a phosphorothioate linkage. The double-stranded oligonucleotide may comprise DNA nucleobases, RNA nucleobases or a mixture of DNA and RNA nucleobases.

In another embodiment, there is provided a method of selectively increasing the expression of a Frataxin transcript comprising contacting a cell having an expanded GAA repeat region with a double-stranded oligonucleotide as described above. The expanded GAA repeat region may contain 60 or more repeats, such as 66 to 1700 repeats. The cell may be contacted with said double-stranded oligonucleotide at about 5-75 nM. The cell may be located in a subject suffering from Friedreich's Ataxia, in which case contacting may comprise administering said double-stranded oligonucleotide by direct administration into the central nervous system, cerebrospinal fluid, or mediated uptake across the blood brain barriers, including administering said double-stranded oligonucleotide more than once. The method may further comprise administering a second therapeutic agent to said subject, such as an agent that modulates histone acetylation, including a histone deacetylase inhibitor.

It is contemplated that any embodiment discussed in this specification can be implemented with respect to any method or composition of the disclosure, and vice versa. Furthermore, compositions of the disclosure can be used to achieve methods of the disclosure.

The use of the word "a" or "an" in the claims and/or the specification may mean "one," but it is also consistent with the meaning of "one or more," "at least one," and "one or more than one."

The phrase "one or more" as found in the claims and/or the specification is defined as 1, 2, 3, 4, 5, 6, 7, 8, 9, 10, or more.

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The disclosure may be better understood by reference to one or more of these drawings in combination with the detailed description of specific embodiments presented herein.

FIGS. 1A-F. RNA-mediated activation of FXN expression. (FIG. 1A) Schematic of repeat expansion within intronic FXN mRNA and binding of AGO:RNA complexes. The longer mutant repeat is predicted to bind more AGO:RNA complexes than the shorter wild-type repeat. (FIG. 1B) Schematic of RNA loop formation at FXN locus and potential to influence histone modification and gene expression (adapted from Groh et al., 2014a). (FIG. 1C) Complementarity of guide strand RNAs (25 nM) to FXN RNA. (FIGS. 1D-E) Effect of anti-GAA duplex RNAs on (FIG. 1D) FXN mRNA and (FIG. 1E) protein expression. (FIG. 1F) A dose response profile of upregulation of FXN protein expression by siGAA. FRDA patient-derived fibroblast cells (GM03816) were used. siExon2 is a duplex siRNA that targets FXN exon and is expected to decrease FXN expression. CM is a negative control RNA that is not complementary to FXN RNA. RNA scramble is a duplex RNA in which the sequences of siGAA and siAAG are mixed to preserve nucleotide composition by alter their order. si5mmAAG is similar to siAAG but has five mismatches relative to the repeat region within FXN mRNA target. Cells were collected at day 3 for RNA extraction and day 4 for protein extraction. **: P<0.01.

(FIG. 2A) Activation of FXN protein expression in FRDA cells (GM03816) and wild-type fibroblast cells (GM02513). (FIGS. 2B-C) Effect of HDAC inhibitor BML210 (5 µM) treatment on expression of (FIG. 2B) FXN mRNA and (FIG. 2C) protein (inset, western analysis) expression in FRDA patient fibroblast cells (GM03816).

(FIG. 3A) RNA immunoprecipitation (RIP) examining the association of Ago2 with FXN pre-mRNA after treatment with 50 nM duplex RNA and analysis by real time PCR. An arrow marks the PCR product of FXN pre-mRNA, which was confirmed by sequencing (FIG. 7) (FIG. 3B) Anti-GAA duplex RNA with central mismatches (siGAA 9.10 mm with mismatches on both strands (SEQ ID NOS: 19-20)) (25 nM) activates FXN expression at a level similar to the analogous fully complementary duplex RNA. siExon3 is a positive control for transfection efficiency targeting exon 3 of FXN. (FIG. 3C) Chromatin immunoprecipitation (ChIP) for RNA polymerase II (RNAP2) using four different primer sets. (FIG. 3D) ChIP for transcription associated histone modification markers H3K4me3, H3K9me2, H3K9me3, H3K9Ac, H3K27me3, and H4Ac (n=4-8). (FIG. 3E) FXN mRNA stability assay. Cells were transfected with duplex RNAs siGAA or CM at 25 nM. 5 µg/mL actinomycin D was added with fresh media three days after transfection and cells were collected at the indicated timepoints. HPRT expression was measured for normalization. All experiments were performed in GM03816 patient-derived cells. *: P<0.05 **: P<0.01.

(FIG. 4A) Structure of LNA. (FIG. 4B) Western analysis of the effect of LNAs with PO backbone on FXN protein expression (FIG. 4C) Quantitation of western analysis (n=2). (FIG. 4D) Western analysis of the effect of LNAs with PS backbone on FXN protein expression (FIG. 4E) Quantitation of quadruplicate western analysis. (FIGS. 4F-G) Quantitative PCR showing effect on FXN mRNA expression of (FIG. 4F) PO LNAs (n=5) or (FIG. 4G) PS LNAs (n=3). PO-control-LNA5 is a negative control LNA with PO backbone that is not complementary to FXN RNA. PO-control-LNA6 has five mismatches relative to the repeat region within FXN RNA target. PS-control-LNA7 is a negative control LNA similar to PO-control-LNA5 but with PS backbone. FRDA patient fibroblast cells (GM03816) were treated with 12.5 nM duplex RNA. Cells were collected at day 3 for RNA extraction and day 4 for protein extraction. All data are presented as mean±STDEV. NT: no treatment; **: P<0.01.

(FIG. 5A) Effects of anti-GAA duplex RNAs on FXN mRNA expression. FRDA patient fibroblast cells (GM03816) were treated with 50 nM of siRNAs. siGAA, siAAG and siAGA are duplex RNAs complementary to the expanded repeat in three different registers. CM is a negative control RNAs that is not complementary to FXN RNA. Data are presented as Mean±STDEVP, n=3. : P<0.01. (FIG. 5B) Effects of anti-GAA duplex RNAs on FXN protein expression. FRDA patient fibroblast cells (GM03816) were treated with 50 nM of siRNAs. siGAA, siAAG are duplex RNAs complementary to the expanded repeat in three different registers. CM is a negative control RNAs that is not complementary to FXN RNA. Data are presented as Mean±SE, n=7. : P<0.01. (FIG. 5C) Dose curve for siGAA on FXN protein expression corresponding to FIG. 1F. FRDA patient fibroblast cells (GM03816) were treated with different concentration of siRNAs. (FIG. 5D) Dose curve for siGAA effects on FXN mRNA expression. FRDA patient fibroblast cells (GM03816) were treated with different concentration of siRNAs. NT: no treatment. Data are presented as Mean±SD, n=2.

FIG. 11. FXN product obtained through Ago2-RIP. The Ago2-associated FXN pre-mRNA products were obtained as present in FIG. 3E, and extracted and sequenced. Dark grey color indicates nucleotides belonging to FXN intron1 region, and light grey color indicates nucleotides belonging to FXN Exon2 region. Ago2 RIPed sequence: SEQ ID NO:54; Ago2 IP sequence: SEQ ID NO:55; Query: SEQ ID NO:56; Sbjct: SEQ ID NO:56.

DETAILED DESCRIPTION

Figure 1A:
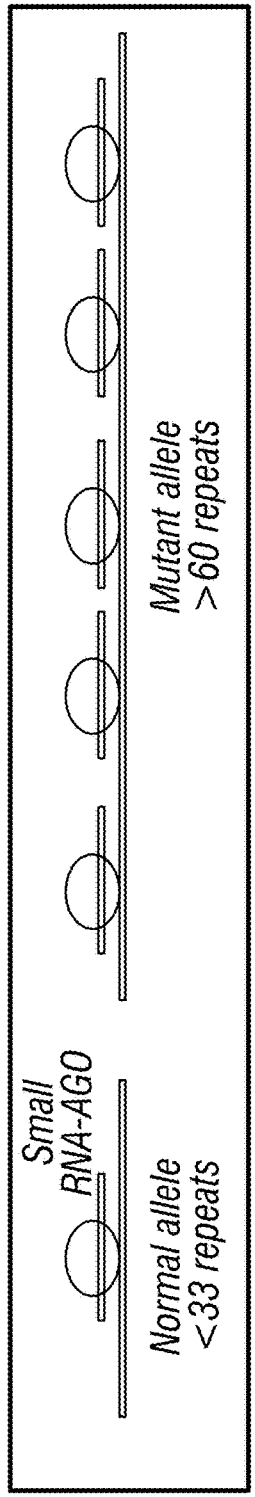

The concept of using nucleic acids as drugs is not new. There has been steady progress over the past twenty years as researchers have acquired a better understanding of nucleic acid chemistry, biology, and pharmacology (Watts and Corey, 2012). Now, fueled by advances in antisense technology, the emergence of RNA interference, and a better understanding of biodistribution to target tissues, modulating gene expression by nucleic acids is becoming a practical option for drug development.

Many clinical trials are ongoing. The most advanced drug is Kynamro, an antisense oligonucleotide from ISIS Pharmaceutical and Genzyme designed to inhibit expression of Apo-B (Adkim et al., 2010ab; Rall et al., 2010; Adkim et al., 2011; Robinson et al., 2013). Data from multiple Phase III trials of systemically administered drug have shown prolonged and dramatic lowering of serum LDL-cholesterol. Monthly intravenous administration of drug dissolved in saline is sufficient and the treatment benefits patients with familial hypocholesterolemia who do not respond adequately to existing drugs. These studies demonstrated that antisense oligonucleotides can enter target tissues in patients and the FDA approved Kynamro in 2013. Several double-stranded RNAs are being evaluated in clinical testing and have demonstrated an ability to inhibit gene target expression in patients (Watts and Corey, 2012). Considerable progress has been made optimizing delivery and lipid formulations now permit potent gene silencing using low (μg/kg) concentrations of duplex. A duplex RNA for treating Transthyretin-mediated amyloidosis is now in Phase III trials (Coelho et al., 2013).

Progress is also being made towards delivery of nucleic acid drugs to the central nervous system. Oligonucleotides and duplex RNAs have been used successfully in primates to inhibit expression of disease genes, demonstrating that distribution throughout the brain and spinal cord can be achieved (Smith et al., 2006; Querbes et al., 2008; Passini et al., 2011; Kordasaiwicz et al., 2012). One Phase I clinical trial of an antisense oligonucleotide against SOD1 for treatment of familial amyotrophic lateral sclerosis has been completed with no serious adverse events reported (Miller et al., 2013).

Modulation of gene expression by duplex RNAs is usually associated with inhibition of gene expression. The inventors' lab and others (Weinberg and Morris, 2013) have shown, however, that duplex RNAs can also be used to enhance transcription of specific target genes (see FIG. 1 for example). To date, the inventors have successfully up-regulated expression of progesterone receptor (PR) (Janowski et al., 2007; Schwartz et al., 2008; Yue et al., 2010), LDL receptor (LDLR) (Matsui et al., 2010), and cyclooxygenase 2 (COX-2) (Matsui et al., 2013). For each of these genes, the mechanism of action involves recognition of an RNA transcript associated with the genomic loci and recruitment of argonaute 2 and other RNAi factors. The inventors have recently shown that Argonaute 2 (Ago2) and other RNAi factors are present in cell nuclei (Gagnon et al., 2014). These data provide precedent for the hypothesis that small RNAs can recognize intronic FXN mRNA and that this recognition can increase levels of FXN RNA and protein.

Among the trinucleotide repeat diseases, Friedreich's Ataxia presents a unique challenge to the use of oligonucleotide-based therapies. As explained above, potential approaches for increasing FXN expression include the use of histone deacetylase inhibitors to reverse the epigenetic changes that contribute to decreased expression, and a recent screen of existing drugs identified the topical anesthetic Dyclonine as an activator of FXN expression, possibly by inducing expression of the transcription factor Nrf2. However, as also noted above, these approaches rely on non-specific gene activation, a potential disadvantage that may disrupt progress in the clinic. Thus, the inventor sought to develop alternative strategies that use synthetic nucleic acids to sequence-specifically recognize expanded GAA mRNA in Friedreich's Ataxia, thereby avoiding the non-specific effects. In the approach described here, the specificity of Watson-Crick base-pairing will drive gene modulation to be directed to FXN only. However, many researchers assume that gene regulation by siRNAs or antisense oligonucleotides is associated with reduced gene expression (gene silencing). In contrast, the inventors' approach exploits the potential for interaction between the expanded GAA repeat with FXN mRNA and FXN genomic DNA to increase FXN protein expression.

The inventors have already developed multiple strategies for achieving allele-selective inhibition of genes containing expanded CAG trinucleotide repeats including mutant huntingtin (HTT) (Huntington disease, HD), ataxin-3 (ATXN-3) (Machado Joseph disease), and atrophin-1 (ATN-1) (Dentatorubral-pallidoluysian atrophy) (Matsui and Corey, 2012). Some of these are described below:

TABLE 1

Publications on allele-selective inhibition of trinucleotide repeat gene expression

| Publ'n | Disease gene targeted | Chemistry used |
| --- | --- | --- |
| Hu, 2009 | HTT | PNA, LNA |
| Hu, 2010 | HTT | Duplex RNA |
| Gagnon, 2010 | HTT | LNA, CeNA, other single-stranded oligos |
| Gagnon, 2011 | HTT | Oligonucleotide-spermine conjugates |
| Hu, 2012 | HTT | Duplex RNA |
| Yu, 2012 | HTT | ss-siRNA |
| Liu, 2013 | HTT, ATXN-3 | Chemically modified dsRNA, abasic RNA |
| Liu, 2013 | ATXN-3 | ss-siRNA |
| Aiba, 2013 | HTT, ATXN-3 | UNA |
| Hu, 2014 | HTT | ss-siRNA |
| Hu, 2014 | ATN-1 | dsRNA, Chem. Mod. dsRNA ss-siRNA, abasic RNA, UNA |

The following disclosure provides further information regarding the implementation of an oligonucleotide-based therapeutic approach for increasing FXN expression, thereby treating Friedreich's Ataxia.

I. DEFINITIONS

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21.sup.st edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2.sup.nd Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein, "2'-F ANA" refers to a 2'-F substituted nucleoside, wherein the fluoro group is in the arabino position.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings);

replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 2'-endo furanosyl nucleosides and RNA surrogates.

As used herein, "2'-endo-furanosyl nucleoside" means an RNA-like nucleoside that comprises a substituted sugar moiety that has a 2'-endo conformation. 2'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "phosphorous moiety" refers to a to monovalent P$^V$ phosphorus radical group. In certain embodiments, a phosphorus moiety is selected from: a phosphate, phosphonate, alkylphosphonate, aminoalkyl phosphonate, phosphorothioate, phosphoramidite, alkylphosphonothioate, phosphorodithioate, thiophosphoramidate, phosphotriester and the like.

The term "phosphate moiety" as used herein, refers to a terminal phosphate group that includes unmodified phosphates (—O—P(=O)(OH)OH) as well as modified phosphates. Modified phosphates include but are not limited to phosphates in which one or more of the O and OH groups is replaced with H, O, S, N(R) or alkyl where R is H, an amino protecting group or unsubstituted or substituted alkyl.

As used herein, "phosphate stabilizing modification" refers to a modification that results in stabilization of a 5'-phosphate moiety of the 5'-terminal nucleoside of an oligonucleotide, relative to the stability of an unmodified 5'-phosphate of an unmodified nucleoside under biologic conditions. Such stabilization of a 5'-phophate group includes but is not limited to resistance to removal by phosphatases. Phosphate stabilizing modifications include, but are not limited to, modification of one or more of the atoms that binds directly to the phosphorus atom, modification of one or more atoms that link the phosphorus to the 5'-carbon of the nucleoside, and modifications at one or more other positions of the nucleoside that result in stabilization of the phosphate. In certain embodiments, a phosphate stabilizing modification comprises a carbon linking the phosphorous atom to the 5'-carbon of the sugar. Phosphate moieties that are stabilized by one or more phosphate stabilizing modification are referred to herein as "stabilized phosphate moieties."

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "single-stranded" means an oligomeric compound that is not hybridized to its complement and which lacks sufficient self-complementarity to form a stable self-duplex.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity is a reduction of a gain-of-function of an expanded repeat-containing nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, the term "expanded repeat-containing RNA" means a mutant RNA molecule having a nucleobase sequence that includes a repeat region having a predetermined number of nucleobases repeats, wherein the presence or length of the repeat region affects the normal processing, function, or activity of the RNA or corresponding protein.

As used herein, the term "corresponding wild-type RNA" means the non-mutant version of the expanded repeat-containing RNA having normal function and activity.

Typically, corresponding wild-type RNA molecules comprise a repeat region which is shorter than that of an expanded repeat-containing RNA.

As used herein, "selectivity" refers to the ability of an antisense compound to exert an antisense activity on a target nucleic acid to a greater extent than on a non-target nucleic acid.

As used herein, "mutant selective" refers to a compound that has a greater effect on a mutant nucleic acid than on the corresponding wild-type nucleic acid. In certain embodiments, the effect of a mutant selective compound on the mutant nucleic acid is 2, 3, 4, 5, 6, 7, 8, 9, 10, 15, 20, 25, 30, 35, 40, 50, 100 or more than 100 times greater than the effect of the mutant selective compound on the corresponding wild-type nucleic acid. In certain embodiments, such selectivity results from greater affinity of the mutant selective compound for the mutant nucleic acid than for the corresponding wild-type nucleic acid. In certain embodiments, selectivity results from a difference in the structure of the mutant compared to the wild-type nucleic acid. In certain embodiments, selectivity results from differences in processing or sub-cellular distribution of the mutant and wild-type nucleic acids. In certain embodiments, some selectivity may be attributable to the presence of additional target sites in a mutant nucleic acid compared to the wild-type nucleic acid. For example, in certain embodiments, a target mutant allele comprises an expanded repeat region comprising more repeats than the wild-type allele. Thus, the wild-type allele has fewer sites available for hybridization of an antisense compound targeting the repeat region. In certain embodiments, a mutant selective compound has selectivity greater than the selectivity predicted by the increased number of target sites. In certain embodiments, the ratio of inhibition of a mutant allele to a wild-type allele is equal to or greater than the ratio of the number of repeats in the mutant allele to the wild-type allele. In certain embodiments, the ratio of inhibition of a mutant allele to a wild-type allele is greater than the ratio of the number of repeats in the mutant allele to the wild-type allele.

As used herein, "gain-of-function activity" means a biological activity attributed to an expanded repeat-containing RNA. For example, an expanded repeat-containing RNA may gain the ability to sequester ribonuclear proteins and impair the normal action of RNA processing in the nucleus (see Cooper, T. (2009) Cell 136, 777-793; O'Rourke, J R (2009) J. Biol. Chem. 284 (12), 7419-7423).

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A)

is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(—N$R_{bb}$)($R_{aa}$)), thiol (—S$R_{bb}$), sulfinyl (—S(O)$R_{bb}$), sulfonyl (—S(O)$_2R_{bb}$) and sulfonimidoyl (—S(O)$_2$N($R_{bb}$)($R_{cc}$) or —N($R_{bb}$)S(O)$_2R_{bb}$), wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between inventorsen an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "parenteral administration," means administration through injection or infusion. Parenteral administration includes, but is not limited to, subcutaneous administration, intravenous administration, or intramuscular administration.

As used herein, "systemic administration" means administration to an area other than the intended locus of activity. Examples or systemic administration are subcutaneous administration and intravenous administration, and intraperitoneal administration.

As used herein, "subcutaneous administration" means administration just below the skin.

As used herein, "intravenous administration" means administration into a vein.

As used herein, "cerebrospinal fluid" or "CSF" means the fluid filling the space around the brain and spinal cord.

As used herein, "administration into the cerebrospinal fluid" means any administration that delivers a substance directly into the CSF.

As used herein, "intracerebroventricular" or "ICV" mean administration into the ventricular system of the brain.

As used herein, "intrathecal" or "IT" means administration into the CSF under the arachnoid membrane which covers the brain and spinal cord. IT injection is performed through the theca of the spinal cord into the subarachnoid space, where a pharmaceutical agent is injected into the sheath surrounding the spinal cord.

II. FRIEDREICH'S ATAXIA

Friedreich's ataxia is an autosomal recessive inherited disease that causes progressive damage to the nervous system. It manifests in initial symptoms of poor coordination such as gait disturbance; it can also lead to scoliosis, heart disease and diabetes, but does not affect cognitive function. The disease progresses until a wheelchair is required for mobility. Its incidence in the general population is roughly 1 in 50,000, making it the most prevalent inherited ataxia. Males and females are affected equally. The estimated carrier prevalence is 1:110. The particular genetic mutation (expansion of an intronic GAA triplet repeat in the FXN gene) leads to reduced expression of the mitochondrial protein frataxin. Over time this deficiency causes the aforementioned damage, as well as frequent fatigue due to effects on cellular metabolism.

The ataxia of Friedreich's ataxia results from the degeneration of nerve tissue in the spinal cord, in particular sensory neurons essential (through connections with the cerebellum) for directing muscle movement of the arms and legs. The spinal cord becomes thinner and nerve cells lose some of their myelin sheath (the insulating covering on some nerve cells that helps conduct nerve impulses).

Symptoms typically begin sometime between the ages of 5 to 15 years, but in Late Onset FA may occur in the 20s or 30s. Symptoms include any combination, but not necessarily all, of the following:

Muscle weakness in the arms and legs
Loss of coordination
Vision impairment
Hearing impairment
Slurred speech
Curvature of the spine (scoliosis)
High plantar arches (pes cavus deformity of the foot)
Diabetes (about 20% of people with Friedreich's ataxia develop carbohydrate intolerance and 10% develop diabetes mellitus)
Heart disorders (e.g., atrial fibrillation, and resultant tachycardia (fast heart rate) and hypertrophic cardiomyopathy)

It presents before 25 years of age with progressive staggering or stumbling gait and frequent falling. Lower extremities are more severely involved. The symptoms are slow and progressive. Long-term observation shows that many patients reach a plateau in symptoms in the patient's early adulthood. On average, after 10-15 years with the disease, patients are usually wheelchair bound and require assistance with all activities of daily living. The following physical signs may be detected on physical examination:

Cerebellar: Nystagmus, fast saccadic eye movements, truncal ataxia, dysarthria, dysmetria.
Lower motor neuron lesion: absent deep tendon reflexes.
Pyramidal: extensor plantar responses, and distal weakness are commonly found.
Dorsal column: Loss of vibratory and proprioceptive sensation occurs.
Cardiac involvement occurs in 91% of patients, including cardiomegaly (up to dilated cardiomyopathy), symmetrical hypertrophy, heart murmurs, and conduction defects. Median age of death is 35 years, while females have better prognosis with a 20-year survival of 100% as compared to 63% in men.
20% of cases are found in association with diabetes mellitus.

Friedreich's ataxia has an autosomal recessive pattern of inheritance. Friedreich's ataxia is an autosomal recessive disorder that occurs when the FXN gene contains amplified intronic GAA repeats. The FXN gene encodes the protein frataxin. GAA repeat expansion causes frataxin levels to be reduced. Frataxin is an iron-binding protein responsible for forming iron-sulfur clusters. One result of frataxin deficiency is mitochondrial iron overload which can cause damage to many proteins. The exact role of frataxin in normal physiology remains unclear. The gene is located on chromosome 9.

The mutant gene contains expanded GAA triplet repeats in the first intron; in a few pedigrees, point mutations have been detected. Because the defect is located in an intron (which is removed from the mRNA transcript between transcription and translation), this mutation does not result in the production of abnormal frataxin proteins. Instead, the mutation causes gene silencing (i.e., the mutation decreases the transcription of the gene) through induction of a heterochromatin structure in a manner similar to position-effect variegation.

The primary site of pathology is spinal cord and peripheral nerves. Sclerosis and degeneration of dorsal root ganglion, spinocerebellar tracts, lateral corticospinal tracts, and posterior columns is also observed. The motor neurons of the spinal cord are spared. In peripheral nerves there is a loss of large myelinated fibres.

Progressive destruction of dorsal root ganglia accounts for thinning of dorsal roots, degeneration of dorsal columns, transsynaptic atrophy of nerve cells in Clarke's column and dorsal spinocerebellar fibers, atrophy of gracile and cuneate nuclei and neuropathy of sensory nerves. The lesion of the dentate nucleus consists of progressive and selective atrophy of large glutamatergic neurons and grumose degeneration of corticonuclear synaptic terminals that contain γ-aminobutyric acid (GABA). Small GABA-ergic neurons and their projection fibers in the dentato-olivary tract survive. Atrophy of Betz cells and corticospinal tracts constitute a second lesion.

Low frataxin levels lead to insufficient biosynthesis of iron-sulfur clusters that are required for mitochondrial electron transport and assembly of functional aconitase and iron dysmetabolism of the entire cell. In normal individuals, the FXN gene encodes frataxin, a mitochondrial matrix protein. This globular protein consisting of two a helices and seven R strands is highly conserved, occurring in all eukaryotes and some prokaryotes. Frataxin has a variety of known functions. Frataxin assists iron-sulfur cluster synthesis in the electron transport chain to ultimately generate adenosine triphosphate (ATP), the energy currency necessary to carry out metabolic functions in cells. Also, frataxin regulates iron transfer in the mitochondria to provide a proper amount of reactive oxygen species (ROS) to maintain normal processes. Without frataxin, the energy in the mitochondria fails, and excess iron causes extra ROS to be created, leading to further cell damage.

A person suffering from Friedreich's Ataxia may require some surgical interventions (mainly for the spine and heart). Often, titanium screws and rods are inserted in the spine to help prevent or slow the progression of scoliosis. As progression of ataxia occurs, assistive devices such as a cane, walker, or wheelchair are required for mobility and independence. Other assistive technology, such as a standing frame, can help reduce the secondary complications of prolonged use of a wheelchair. The goal of surgery is to keep the patient ambulatory as long as possible.

In many cases, patients experience significant heart conditions as the well. These conditions, fortunately, are much more treatable, and are often countered with ACE inhibitors such as enalapril or lisinopril and other heart medications such as digoxin.

Persons with Friedreich's ataxia may also benefit from a conservative treatment approach for the management of symptoms. Health professionals educated in neurological conditions, such as physical therapists and occupational therapists, can prescribe an exercise program tailored to maximize function and independence. To address the ataxic gait pattern and loss of proprioception typically seen in persons with Friedreich's ataxia, physical therapists can use visual cueing during gait training to help facilitate a more efficient gait pattern. The prescription of an assistive device along with gait training can also prolong independent ambulation.

Low intensity strengthening exercises should also be incorporated to maintain functional use of the upper and lower extremities. Fatigability should be monitored closely. Stabilization exercises of the trunk and low back can help with postural control and the management of scoliosis. This is especially indicative if the person is non-ambulatory and requires the use of a wheelchair. Balance and coordination training using visual feedback can also be incorporated into activities of daily living. Exercises should reflect functional tasks such as cooking, transfers and self-care. Along with gait training, balance and coordination training should be developed to help minimize the risk of falls. Stretching exercises can be prescribed to help relieve tight musculature due to scoliosis and pes cavus deformities.

Idebenone, a prescription medicine, was recently removed from the Canadian market due to lack of effectiveness. RG2833 is a histone deacetylase inhibitor originally developed by Repligen but later acquired by BioMarin Pharmaceutical in January 2014. The first human trials with this compound began in 2012. Nicotinamide administration on patients was associated with a sustained improvement in frataxin concentrations towards those seen in asymptomatic carriers during 8 the weeks of daily dosing. The daily oral administration of nicotinamide at the dosage of 3.8 g would result in a 1.5-times increase and 7-5 g in a doubling of frataxin protein concentration.

III. OLIGONUCLEOTIDE AGENTS

The oligonucleotide agents of the present disclosure are double-stranded oligonucleotides of 13 to 22 nucleobases in length and having a repeating tri-nucleobase sequence comprising (i) GAA or CUU or (ii) AAG or UUC. The length of the oligonucleotide may be 13, 14, 15, 16, 17, 18, 19, 20, 21 or 22 nucleobases. The oligonucleotides may, in particular, be RNA and include one or more modified and/or non-natural nucleobases. The oligonucleotide may contain DNA as well as RNA nucleobases, such as terminal thymidine residues. In particular, the oligonucleotides may be represented by the specific sequences:

```
                                          (SEQ ID NO: 1)
            GAAGAAGAAGAAGAAGdTdT (SEQ ID NO: 2)
            AAGAAGAAGAAGAAGAdTdT
```

Another design consideration is the placement of 1, 2, 3, 4 or 5 "mismatches" in the double-stranded RNA as compared to the target sequence. In one embodiment, the mismatches are generally "centrally located" in the RNA, i.e., not located within the first two or last two bases of the RNA. A more restrictive definition of centrally located would be the center 3-4 bases, or in the center base (for an odd number of bases) or one or both of the center bases (for an even number of bases). More particularly, on a nucleic acid of at least 15 residues in length, there should be at least 7 residues flanking each side of the mismatch base, or on a nucleic acid of at least 16 residues in length, there should be at least 7 residues flanking two adjacent mismatched bases. Though any mismatch is useful, of particular interest are purine mismatches, such as introducing an adenosine base into the guide strand.

Another consideration is to avoid multiple changes in the "seed" sequence of the double-stranded RNA, i.e., the first 8 bases. Thus, in a double-stranded RNA of at least 19 bases, there would no or one mismatches in 2-8 bases, and 1-5 mismatches in bases 9-14, or in bases 15 to the 3'-terminus. In other words, with respect to multiple mismatches, these can be either in the guide strand, or in both strands, and only one mismatch should occur in the seed region. In addition, to mismatches, it is contemplated that the guide strand may contain a base insertion with respect to the passenger strand.

In addition to double-stranded RNAs, ss-siRNAs are a new approach to gene silencing in which single-stranded RNA is chemically modified to enable it to be stable in vivo while retaining the ability to engage the RNAi machinery (Lima et al., 2012). The inventors have previously shown that anti-CAG ss-siRNAs can be active towards inhibiting expression of CAG repeat containing genes in cell culture and the central nervous system of HD model mice. ss-siRNAs are attractive candidates for testing because, in contrast to duplex RNA, they are single-stranded and may possess better biodistribution and activity in vivo. Thus, the inventors contemplate the application of ss-siRNAs as GAA/CUU and AAG/UUC repeat targeting agents.

Figure 8:
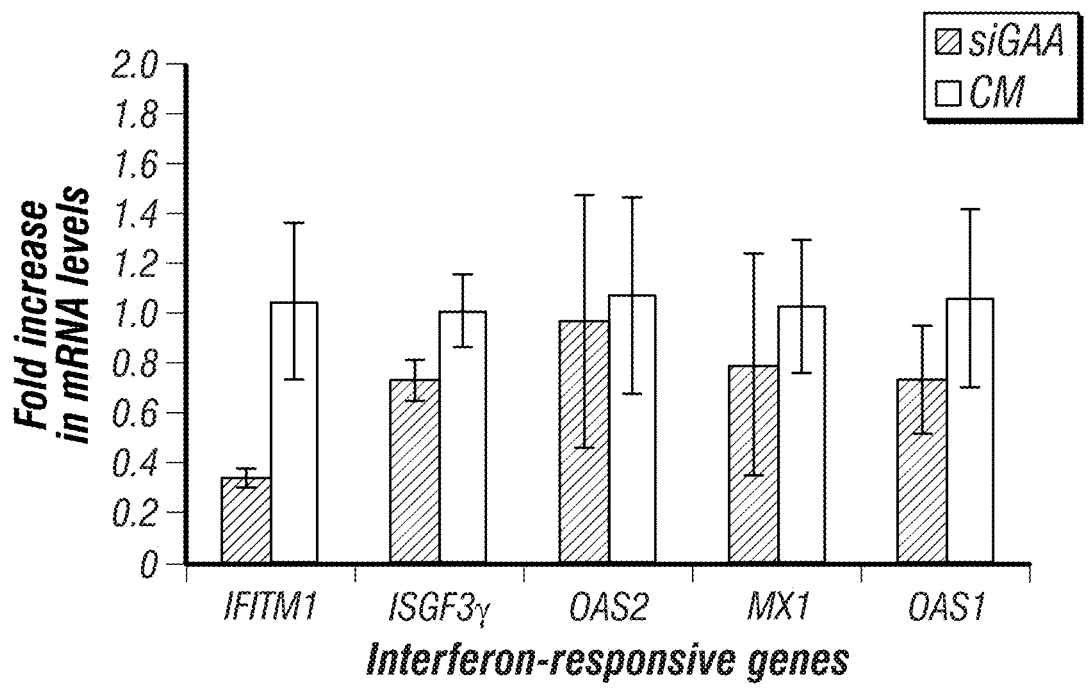
FIG. 8. siGAA does not induce expression of interferon responsive genes. qPCR data showing no significant impact of siGAA compared with CM control on the mRNA expression of interferon responsive genes. FRDA patient fibroblast cells (GM03816) were treated with 25 nM of siRNAs, and were collected for qPCR 3 days after transfection. Data are presented as Mean±SD, n=2. GAPDH was used as internal control for the interferon responsive genes.
Figure 10:
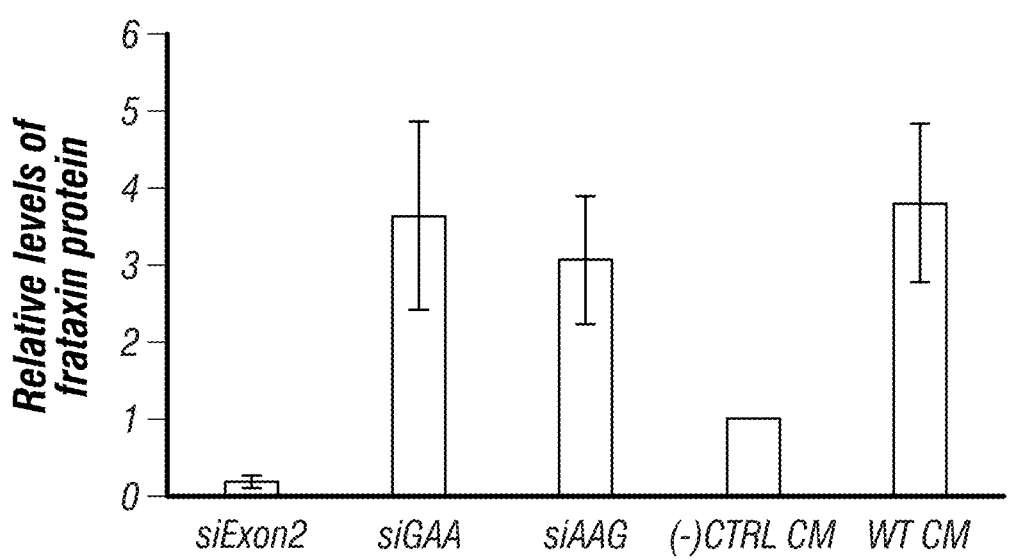
FIG. 10. Comparison of RNA-mediated activation of FXN expression in patient cells to FXN expression in normal cells. FRDA patient fibroblast cells (GM03816) and wild-type fibroblast cells (GM02513) were treated with 50 nM of siRNAs. Data are presented as Mean±SD, n=3.

Single-stranded antisense oligonucleotides (ASOs) should also bind directly to the GAA repeat. ASOs will not require the RNAi machinery and are a different strategy for silencing gene expression. Once bound, the ASOs will disrupt interactions between the RNA and chromatin at the FXN locus and lead to activation of FXN expression. The inventors contemplate ASOs substituted with locked nucleic acids (LNAs). LNA nucleotides are constrained by a bond between the 2' and 4' positions of the ribose ring (FIG. 8). This constraint "locks" the nucleotide into a position that is ideal for base-pairing and the introduction of a handful of LNA nucleotides into an ASO can tailor the affinity of an ASO for optimal success in many applications. Thus, the inventors also contemplate the application of ASOs as GAA/CUU and AAG/UUC repeat targeting agents.

Commercially available equipment routinely used for the support media based synthesis of oligomeric compounds and related compounds is sold by several vendors including, for example, Applied Biosystems (Foster City, Calif.), General Electric, as well as others. Suitable solid phase techniques, including automated synthesis techniques, are described in Scozzari and Capaldi, "Oligonucleotide Manufacturing and Analysic Processes for 2'-O-(2-methoxyethyl-Modified Oligonucleotides" in Crooke, S. T. (ed.) ANTISENSE THERAPEUTICS (2008).

IV. MODIFIED NUCLEOBASES

In certain embodiments, compounds of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH (CH$_2$OCH$_3$)—O-2', and analogs thereof (see, e.g., U.S. Pat. No. 7,399,845, issued on Jul. 15, 2008); 4'-C(CH$_3$)(CH$_3$)—

O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya et al., J. Org. Chem., 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein:

x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and
each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Methoxy(ethyleneoxy) (4'-CH(CH$_2$OMe)-O-2') BNA (also referred to as constrained MOE or cMOE).

Additional bicyclic sugar moieties are known in the art, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 5561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the .alpha.-L configuration or in the .beta.-D configuration. Previously, α-L-methyleneoxy (4'-CH$_2$—O-2') bicyclic nucleosides have been incorporated into antisense oligonucleotides that showed antisense activity (Frieden et al., Nucleic Acids Research, 2003, 21, 6365-6372).

In certain embodiments, substituted sugar moieties comprise one or more non-bridging sugar substituent and one or more bridging sugar substituent (e.g., 5'-substituted and 4'-2' bridged sugars; PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US20050130923, published on Jun. 16, 2005) and/or the 5' position. By way of additional example, carbocyclic bicyclic nucleosides having a 4'-2' bridge have been described (see, e.g., Freier et al., Nucleic Acids Research, 1997, 25(22), 4429-4443 and Albaek et al., J. Org. Chem., 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. Bioorg. & Med. Chem. (2002) 10:841-854), and fluoro HNA (F-HNA).

In certain embodiments, the modified THP nucleosides of Formula VII are provided wherein q$_1$, q$_2$, q$_3$, q$_4$, q$_5$, q$_6$ and q$_7$ are each H. In certain embodiments, at least one of q$_1$, q$_2$, q$_3$, q$_4$, q$_5$, q$_6$ and q$_7$ is other than H. In certain embodiments, at least one of q$_1$, q$_2$, q$_3$, q$_4$, q$_5$, q$_6$ and q$_7$ is methyl. In certain embodiments, THP nucleosides of Formula VII are provided wherein one of R$_1$ and R$_2$ is F. In certain embodiments, R$_1$ is fluoro and R$_2$ is H, R$_1$ is methoxy and R$_2$ is H, and R$_1$ is methoxyethoxy and R$_2$ is H.

Many other bicyclo and tricyclo sugar surrogate ring systems are also known in the art that can be used to modify nucleosides for incorporation into antisense compounds (see, e.g., review article: Leumann, J. C, Bioorganic & Medicinal Chemistry, 2002, 10, 841-854).

Combinations of modifications are also provided without limitation, such as 2'-F-5'-methyl substituted nucleosides (see PCT International Application WO2008/101157 Published on Aug. 21, 2008 for other disclosed 5',2'-bis substituted nucleosides) and replacement of the ribosyl ring oxygen atom with S and further substitution at the 2'-position (see U.S. Patent Publication US20050130923, published on Jun. 16, 2005) or alternatively 5'-substitution of a bicyclic nucleic acid (see PCT International Application WO2007/

134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

In certain embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and 0-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., Angewandte Chemie, International Edition, 1991, 30, 613; and those disclosed by Sanghvi, Y. S., Chapter 15, Antisense Research and Applications, Crooke, S. T. and Lebleu, B., Eds., CRC Press, 1993, 273-288.

Representative United States Patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, each of which is herein incorporated by reference in its entirety.

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), a or R such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-5-CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-5-tritylthiol (Manoharan et al., Ann. N.Y. Acad. Sci., 1992, 660, 306; Manoharan et al., Bioorg. Med. Chem. Let., 1993, 3, 2765); a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylaminocarbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

V. PHARMACEUTICAL FORMULATIONS

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals. One will generally desire to employ appropriate salts, buffers, and lipids to render delivery of the oligonucleotides to allow for uptake by target cells. Such methods an compositions are well known in the art, for example, as disclosed in U.S. Pat. Nos. 6,747,014 and 6,753,423. Compositions of the present disclosure comprise an effective amount of the oligonucleotide to cells, dissolved or dispersed in a pharmaceutically acceptable carrier or medium.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents, liposomes, cationic lipid formulations, microbubble nanoparticles, and the like. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. This includes oral, nasal, buccal, or topical. Alternatively, administration may be by intradermal, subcutaneous, intramuscular, intraperitoneal or intravenous injection, or introduction into the CNS, such as into spinal fluid. Such compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, lipids, nanoparticles, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the oligonucleotides of the present disclosure may be incorporated with excipients. The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Of particular interest to the present disclosure is the use of lipid delivery vehicles. Lipid vehicles encompass micelles, microemulsions, macroemulsions, liposomes, and similar carriers. The term micelles refers to colloidal aggregates of amphipathic (surfactant) molecules that are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100. Microemulsions are essentially swollen micelles, although not all micellar solutions can be swollen to form microemulsions. Microemulsions are thermodynamically stable, are formed spontaneously, and contain particles that are extremely small. Droplet diameters in microemulsions typically range from 10 100 nm. In contrast, the term macroemulsions refers to droplets with diameters greater than 100 nm. Liposomes are closed lipid vesicles comprising lipid bilayers that encircle aqueous interiors. Liposomes typically have diameters of 25 nm to 1 µm.

In one embodiment of a liposome formulation, the principal lipid of the vehicle may be phosphatidylcholine. Other useful lipids include various natural (e.g., tissue derived L-α-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a secondary lipid. Such secondary helper lipids may be non-ionic or uncharged at physiological pH, including non-ionic lipids such as cholesterol and DOPE (1,2-dioleolylglyceryl phosphatidylethanolamine). The molar ratio of a phospholipid to helper lipid can range from about 3:1 to about 1:1, from about 1.5:1 to about 1:1, and about 1:1.

Another specific lipid formulation comprises the SNALP formulation, containing the lipids 3-N-[(ω methoxypoly (ethylene glycol)$_{2000}$) carbamoyl-]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar % ratio.

Exemplary amounts of lipid constituents used for the production of the liposome include, for instance, 0.3 to 1 mol, 0.4 to 0.6 mol of cholesterol; 0.01 to 0.2 mol, 0.02 to 0.1 mol of phosphatidylethanolamine; 0.0 to 0.4 mol, or 0-0.15 mol of phosphatidic acid per 1 mol of phosphatidylcholine.

Liposomes can be constructed by well-known techniques. Lipids are typically dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires several minutes depending upon conditions, kind, and quality of the sonicator. Commonly, lipid concentrations are 1 mg/ml of aqueous phase, but could be higher or lower by about a factor of ten.

Lipids, from which the solvents have been removed, can be emulsified by the use of a homogenizer, lyophilized, and melted to obtain multilamellar liposomes. Alternatively, unilamellar liposomes can be produced by the reverse phase evaporation method (Szoka and Papahadjopoulos, 1978). Unilamellar vesicles can also be prepared by sonication or extrusion. Sonication is generally performed with a bath-type sonifier, such as a Branson tip sonifier (G. Heinemann Ultrashall and Labortechnik, Schwabisch Gmund, Germany) at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilamellar liposomal vesicles of specific sizes. The liposomes can also be formed by extrusion through an asymmetric ceramic filter, such as a Ceraflow Microfilter (commercially available from the Norton Company, Worcester, Mass.).

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size. For use in the present disclosure, liposomes have a size of about 0.05 microns to about 0.5 microns, or having a size of about 0.05 to about 0.2 microns.

VI. METHODS OF DELIVERING OLIGONUCLEOTIDES

In certain embodiments, the oligonucleotide compounds and compositions as described herein are administered parenterally. In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, oligonucleotide compounds and compositions are delivered to the CNS. In certain embodiments, oligonucleotide compounds and compositions are delivered to the cerebrospinal fluid. In certain embodiments, oligonucleotide compounds and compositions are administered to the brain parenchyma. In certain embodiments, oligonucleotide compounds and compositions are delivered to an animal by intrathecal administration, or intracerebroventricular administration. Broad distribution of oligonucleotide compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

In certain embodiments, delivery of an oligonucleotide compound or composition described herein can affect the pharmacokinetic profile of the oligonucleotide compound or composition. In certain embodiments, injection of a oligonucleotide compound or composition described herein, to a targeted tissue improves the pharmacokinetic profile of the oligonucleotide compound or composition as compared to infusion of the oligonucleotide compound or composition. In a certain embodiment, the injection of an oligonucleotide compound or composition improves potency compared to broad diffusion, requiring less of the compound or composition to achieve similar pharmacology. In certain embodiments, similar pharmacology refers to the amount of time that a target mRNA and/or target protein is down-regulated (e.g., duration of action). In certain embodiments, methods of specifically localizing a pharmaceutical agent, such as by bolus injection, decreases median effective concentration ($EC_{50}$) by a factor of about 50 (e.g., 50-fold less concentration in tissue is required to achieve the same or similar pharmacodynamic effect). In certain embodiments, methods of specifically localizing a pharmaceutical agent, such as by bolus injection, decreases median effective concentration ($EC_{50}$) by a factor of 20, 25, 30, 35, 40, 45 or 50.

In certain embodiments, delivery of an oligonucleotide compound or composition, as described herein, to the CNS results in 47% down-regulation of a target mRNA and/or target protein for at least 91 days. In certain embodiments, delivery of a compound or composition results in at least 25%, at least 30%, at least 35%, at least 40%, at least 45%, at least 50%, at least 55%, at least 60%, at least 65%, at least 70%, or at least 75% down-regulation of a target mRNA and/or target protein for at least 20 days, at least 30 days, at least 40 days, at least 50 days, at least 60 days, at least 70 days, at least 80 days, at least 85 days, at least 90 days, at least 95 days, at least 100 days, at least 110 days, at least 120 days. In certain embodiments, delivery to the CNS is by intraparenchymal administration, intrathecal administration, or intracerebroventricular administration.

In certain embodiments, an oligonucleotide is delivered by injection or infusion once every week, every two weeks, every month, every two months, every 90 days, every 3 months, every 6 months, twice a year or once a year.

VII. COMBINATION THERAPIES

It is common in many fields of medicine to treat a disease with multiple therapeutic modalities, often called "combination therapies." In the present application, the inventors contemplate using combination therapies to treat Friedreich's Ataxia. Such combinations will include the oligonucleotides according to the present disclosure, along with one or more "standard" therapeutic modalities.

Thus, to treat Friedreich's Ataxia, one would generally contact a target cell or subject with an oligonucleotide and at least one other therapy. These therapies would be provided in a combined amount effective to achieve a reduction in one or more disease parameter. This process may involve contacting the subjects with the both agents/therapies at the same time, e.g., using a single composition or pharmacological formulation that includes both agents, or by contacting the cell/subject with two distinct compositions or formulations, at the same time, wherein one composition includes the oligonucleotide and the other includes the other agent.

Alternatively, the oligonucleotide may precede or follow the other treatment by intervals ranging from minutes to weeks. One would generally ensure that a significant period of time did not expire between each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the oligonucleotide or the other therapy will be desired. Various combinations may be employed, where the oligonucleotide is "A," and the other therapy is "B," as exemplified below:

| A/B/A   | B/A/B   | B/B/A   | A/A/B   | B/A/A   | A/B/B   | B/B/B/A | B/B/A/B |
| A/A/B/B | A/B/A/B | A/B/B/A | B/B/A/A | B/A/B/A | B/A/A/B | B/B/B/A |         |
| A/A/A/B | B/A/A/A | A/B/A/A | A/A/B/A | A/B/B/B | B/A/B/B | B/B/A/B |         |

Other combinations are contemplated. As discussed above, ACE inhibitors idebenone, RG2833 a histone deacetylase inhibitor, nicotinamide, physical therapy and surgery have been used to treat Friedreich's Ataxia and can be used in combination with the oligonucleotide therapies described herein.

VIII. KITS

Any of the compositions described herein may be comprised in a kit. In a non-limiting example, an oligonucleotide targeting a tri-nucleobase repeat is included in a kit. The kit may further include a sterile buffer to facilitate dilution. The kit may also include one or more devices for delivery, such as a syringe, catheter, inhaler or aerosol delivery device.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present disclosure also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the active agent may be provided as dried powder(s). When reagents and/or components are provided as a dry powder, the powder can be reconstituted by the addition of a suitable solvent. It is envisioned that the solvent may also be provided in another container means. Such kits may also include components that preserve or maintain the active agent that protect against its degradation.

The kits of the present disclosure will also typically include a means for containing the vials in close confinement for commercial sale, such as, e.g., injection and/or blow-molded plastic containers into which the desired vials are retained. A kit will also include instructions for employing the kit components as well the use of any other reagent not included in the kit. Instructions may include variations that can be implemented.

It is contemplated that such reagents are embodiments of kits of the disclosure. Such kits, however, are not limited to the particular items identified above and may include any reagent used for the manipulation or delivery of oligonucleotides.

IX. EXAMPLES

The following examples are included to demonstrate certain non-limiting aspects of the disclosure. It should be appreciated by those of skill in the art that the techniques disclosed in the examples which follow represent techniques discovered by the inventor to function well in the practice of the disclosure. However, those of skill in the art should, in light of the present disclosure, appreciate that many changes can be made in the specific embodiments which are disclosed and still obtain a like or similar result without departing from the spirit and scope of the disclosure.

Example 1—Background and Theory

The inventors have used a diverse group of synthetic nucleic acid oligonucleotides and nucleic acid mimics including peptide nucleic acid (PNA), single-stranded locked nucleic acid (LNA) and other single-stranded antisense oligonucleotides, duplex RNA, and single-stranded silencing RNAs (ss-siRNAs, chemically modified single stranded RNAs that function through the RNAi pathway (Lima, 2012). The inventors have also successfully used duplex RNAs to target the expanded hexanucleotide repeat within the C9orf72 gene to inhibit foci formation by C9orf72 RNA (Hu, unpublished). ss-siRNAs administered by intraventricular injection inhibit expression of mutant huntingtin protein (HTT) in Huntington Disease (HD) model mice, demonstrating the potential for translation of nucleic acids to in vivo targets within the central nervous system (Yu, 2012; Hu, 2014). The conclusion reinforced by multiple studies is that allele-selective recognition of trinucleotide repeats can be readily achieved by many different designed nucleic acids.

Figure 2A:
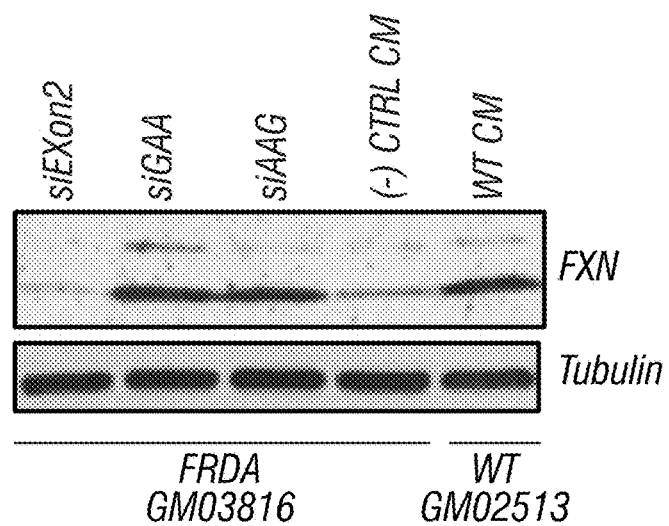
FIGS. 2A-C. Comparison of RNA-mediated activation of FXN expression in patient cells to FXN expression in normal cells and FXN activation by a histone deacetylase inhibitor.

In addition, the inventors have carried out extensive studies to characterize allele-selective recognition of trinucleotide repeat genes by duplex RNAs (Hu et al., 2012). The inventors have found that recognition involves RNAi factors like Ago2 and GW182 and cooperative interactions consistent with binding of multiple RNAs to the expanded repeat. The simplest explanation for allele selectivity is that the mutant alleles have more binding sites for recognition of RNA than do the wild-type alleles. For the expanded repeat within frataxin mRNA, the mutant allele has greater than 60 repeats while the normal allele has less than 33 and most often less than 12 repeats. A schematic showing the potential for binding multiple RNAs to the expanded FXN repeat is shown in FIG. 2.

Figure 3A:
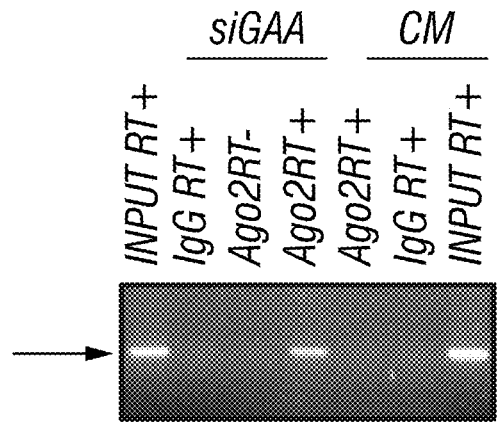
FIGS. 3A-E. Mechanism of FXN activation by repeat-targeted duplex RNAs.
Figure 3B:
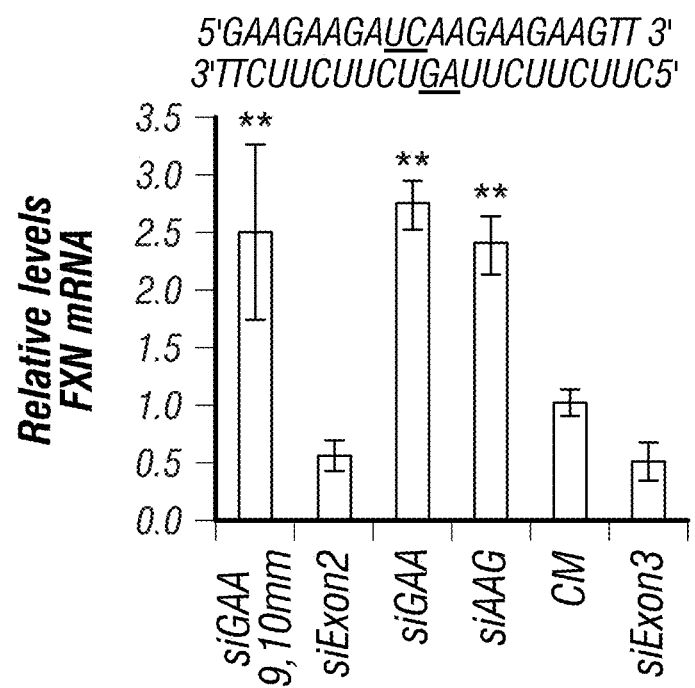

It has been proposed that expanded GAA repeat within the nascent FXN transcript may bind to expanded GAA repeat within genomic DNA to form an R-loop (Ohshima et al., 1998; Bidichandani et al., 1998; Grabczyk et al., 2007; 2008; Groh et al., 2014a; Groh et al., 2014b). This R-loop may then interfere with transcription and reduce FXN expression (FIG. 3B). The inventors hypothesize that oligonucleotides can bind to expanded repeat RNA and block R-loop formation, thereby removing the trigger for transcriptional silencing.

Expanded repeats are known to bind to proteins (Udd and Krahe, 2012) and protein may bind to the nascent FXN transcript while it is in close proximity to genomic DNA, triggering histone modifications that lead to reduced expression (FIG. 3B). By targeting the expanded repeat with duplex RNAs the inventors will: 1) disrupt recognition by previously bound cellular proteins and 2) recruit Ago2 and other RNAi factors. As noted above, the inventors have previously observed transcriptional activation when duplex RNAs are targeted to transcript that overlap the promoters for progesterone receptor (PR) (Schwartz, 2008), LDL receptor (LDLR) (Matsui et al., 2010), and cyclooxgenase 2 (COX-2) (Matsui et al., 2013). These activating RNAs alter protein binding and induce changes in histone modification, providing a precedent for the possibility that duplex RNAs might affect gene expression similarly at the FXN locus.

The inventors hypothesized that: 1) double-stranded RNAs or antisense oligonucleotides can interact with the intronic expanded repeat within mutant FXN pre-mRNA; 2) once this association occurs, binding will block the expanded RNA from forming interactions with FXN DNA directly or indirectly with proteins; and 3) by blocking these interactions, the inventors will reverse silencing and increase production of FXN protein.

Example 2—Materials and Methods

Tissue culture and transfection of synthetic nucleic acids. Fibroblast cells (Coriell Institute, GM03816 and GM02513) were cultured in minimum essential medium (MEM) supplemented with 10% FBS and 1% NEAA. All cells were grown at 37° C. in 5% $Co_2$. Lipofectamine RNAiMAX (Invitrogen) was used to transfect siRNAs or LNA following the manufacturer's recommended protocol in OptiMEM low serum medium (Invitrogen). Growth media was changed to full medium after 24 h. Transfected cells were harvested 72 h after transfection for RNA extraction and qPCR analyses, and 96 h after transfection for western blot analysis. Sequences of siRNAs and RNAs used in these studies are listed in Table S1 and Table S2, respectively.

RNA immunoprecipitation. FRDA patient fibroblast cells (GM03816) were treated with 50 nM of siRNAs CM (control dsRNA) or siGAA. Cells were grown in 15 cm dishes harvested three days after transfection Cell were harvested by treating with trypsin-EDTA solution (Invitrogen), washing with PBS, and then resuspended in ice-cold hypotonic lysis buffer (HLB) (10 mM Tris-HCl, pH 7.5, 10 mM NaCl, 3 mM MgCl$_2$, 0.3% NP-40). After incubation on ice for 15 min and pipetting and vortexing, lysate was spun at 4° C. at 800×g for 5 min to separate nuclei from cytoplasm. Pelleted nuclei were washed 3× with ice-cold HLB followed by 5 min incubation on ice, pipetting and vortexing, then centrifugation at 4° C. at 100×g for 2 min.

Nuclei were resuspended in ice-cold nuclear lysis buffer (NLB) (20 mM Tris-HCl, pH 7.5, 0.15 M NaCl, 3 mM MgCl$_2$, 0.3% NP-40, 10% glycerol) supplemented with 1% Protease Inhibitor Cocktail (Roche), 5 µl/mL RNaseIn (Promega) at a final of 0.5 mL/75 mg of original wet cell pellet weight. Nuclei were sonicated on ice at 20% power 3× for 15 sec in 4 mL volumes. After high-speed centrifugation at 4° C. to remove insoluble cell debris, the soluble fraction was kept as nuclear extract.

All extracts were aliquoted, flash-frozen in liquid nitrogen, and stored at −80° C. RNA immunoprecipitation (RIP) was performed as previously described (Chu et al., 2010; Liu et al., 2012), using anti-AGO2 (Wako) and mouse nonspecific IgG antibodies. Real-time polymerase chain reaction was performed to measure the expression of the levels of AGO2-associated FXN pre-mRNA using primer pairs targeting the region of intron1-exon2 (In1Ex2), with amplification of HPRT as internal control. qPCR products were resolved on 1.5% gels (FIG. 3A). The bands visible were subsequently extracted and sequenced. Primers are listed in Table S2.

Western blot analysis. Cell extracts were prepared using lysis buffer supplemented with 1% Protease Inhibitor Cocktail Set I (Calbiochem) as described previously (Punga & Buhler, 2010). Protein was separated on 4-20% gradient or 15% SDS-PAGE TGX pre-cast gels (BioRad). After gel electrophoresis, proteins were transferred to nitrocellulose membrane (Hybond-C Extra, GE Healthcare Life Sciences) at 100 V for 45-60 min. Membranes were blocked for 30 min at room temperature with 5% milk protein in PBS+0.05% TWEEN-20 (PBST).

Blocked membranes were incubated with the primary antibodies at 4° C. in PBST and 5% milk with rocking overnight: anti-FXN at 1:300 (Abcam, ab110328), anti-tubulin at 1:6000-10000 (Sigma-Aldrich, T5201). After primary antibody incubation, membranes were washed 3 times for 5 min at room temperature with PBST then incubated for 30-45 min at room temperature with HRP-conjugated anti-mouse (Jackson Laboratories, 715-035-150) in PBST+5% milk. Membranes were washed again 3× for 15 min in PBST at room temperature, then protein bands visualized using SuperSignal West Pico Chemiluminescent Substrate (Thermo Scientific). For quantification of protein levels from Western blots of cellular fractions, films were scanned and bands quantified using ImageJ.

Quantitative PCR. Identical volumes of RNA (representing approximately the same number of cells and ranging from 1-2 µg of RNA) were treated with 2 units of DNase I (Worthington) in DNase I buffer (10 mM Tris-HCl, pH 7.0, 10 mM NaCl, 2 mM MgCl$_2$, 0.5 mM CaCl$_2$)) for 15 min at room temperature to degrade any genomic DNA contamination. Afterwards, DNase I heat-inactivated at 75° C. for 10 min. Treated RNAs were reverse-transcribed using the High Capacity cDNA Reverse Transcription Kit (Applied Biosystems). Quantitative PCR (qPCR) was performed using SYBR Supermix (Biorad) with ~50 ng of cDNA as template. Data were normalized relative to measured HPRT levels.

Chromatin Immunoprecipitation (ChIP). FRDA GM03816 cells were transfected with siGAA or CM and cultured as described above for RNA immunoprecipitation. Three days after transfection, cells were crosslinked with 1% formaldehyde and harvested by scraping. Cell nuclei were isolated by washing twice with hypotonic lysis buffer (5 ml×2; 10 mM Tris-HCl (pH 7.5), 10 mM NaCl, 3 mM MgCl$_2$, 0.5% NP-40). Nuclei were lysed in nuclear lysis buffer (1 ml; 50 mM Tris-HCl (pH 8.1), 10 mM EDTA, 1% SDS, 1× protease inhibitors cocktail (Roche) and then sonicated (3 pulses, 20% power, 20 s). Each sample was centrifuged at 13000 rpm for 10 min at 4° C. and the supernatant was kept as nuclear lysate. The nuclear lysate (40µ) was incubated overnight with antibodies in immunoprecipitation buffer (1 ml; 16.7 mM Tris-HCl (pH 8.1), 167 mM NaCl, 1.2 mM EDTA, 1.1% Triton X-100, 0.01% SDS, 1× protease inhibitor cocktail). The antibodies used for ChIP are as follows: anti-RNAP2 (Millipore, 05-623), anti-H3K4me3 (Abcam, ab8580), anti-H3K9me2 (Millipore, 17-648), anti-H3K9me3 (Millipore, 17-625), anti-H3K27me3 (Millipore, 17-449), anti-H3K9Ac (Millipore, 17-658), anti-H4Ac (K5, 8, 12, 16, Millipore, 06-598), normal rabbit IgG (Millipore, 12-370), and normal mouse IgG (Millipore, 12-371). After that, each sample was incubated with 50 µL of Protein A Plus Protein G Agarose Beads (Calbiochem) at 4° C. for 3 h. The beads were washed with low salt buffer (20 mM Tris-HCl (pH 8.1), 150 mM NaCl, 2 mM EDTA, 1% Triton X-100, 0.1% SDS), high salt buffer (see low salt but with 500 mM NaCl), LiCl solution (10 mM Tris-HCl (pH 8.1), 1 mM EDTA, 1% deoxychorate, 1% NP-40, 0.25 M LiCl), and TE buffer (pH 8.0). Protein was eluted twice with 250 µL of elution buffer (0.1 M NaHCO$_3$, 1% SDS) for 5 min at room temperature. Reverse crosslinking was performed by adding NaCl to 200 mM and heating at 65° C. for 2 h 30 min. Each sample was treated with proteinase K (20 µg) at 42° C. for 50 min, followed by phenol extraction using an equal volume of phenol/chloroform/isoamyl alcohol. DNA in the aqueous layer was precipitated using 1/10 volume 3 M sodium acetate (pH 5.5), 2.2 volumes 100% ethanol, and glycogen (30 µg). The pellets were dissolved in 100 µL of nuclease free water and then used as templates for qPCR. The sequences of the qPCR primers are presented in Table S3.

HDAC inhibitor and mRNA stability assay. Histone deacetylase inhibitor BML-210 (Abcam) (5 µM) was applied to FRDA fibroblast cells (GM03816) by following the procedure described in Herman et al (2006)[27]. Cells were collected for qPCR and Western blot analyses as mentioned above. For mRNA stability assay, cells were transfected with siGAA or CM as above, and 5 µg/mL actinomycin D (Sigma) was added with fresh media 3 day after transfection, and cells were collected at the indicated time points for RNA extraction and qPCR analysis.

DNA immunoprecipitation (DIP) analysis. FRDA patient fibroblast cells (GM03816) were treated with 50 nM siRNAs CM and siGAA as above. Cells were collected 2 day afternoon transfection. Cell lysis and nuclei collection follow were as described (Gagnon et al., 2014). The purified nuclei were lysed and further processed for IP as described (Groh et al., 2014a), except the proteinase K (Invitrogen) treatment were carried out at 42° C. DIP was performed by DNA-RNA specific antibody S9.6 (Kerafast) following published methods (Groh et al., 2014a). qPCR analyses for the immunoprecipitated and control DNAs were performed and analyzed as described (Groh et al., 2014a; Loomis et al., 2014). The primer pairs are: FXNin1UP (F: GAAACC-CAAAGAATGGCTGTG (SEQ ID NO: 3); R: TTCCCTCCTCGTGAAACACC (SEQ ID NO: 4)); ZNF554 (F: CGGGGAAAAGCCCTATAAAT (SEQ ID NO: 5); R: TCCACATTCACTGCATTCGT (SEQ ID NO:

6); MYADM (F: CGTAGGTGCCCTAGTTGGAG (SEQ ID NO: 7); R: TCCATTCTCATTCCCAAACC (SEQ ID NO: 8)). FXNin1UP is the region adjacent to the GAA repeat region of FXN intron 1. ZNF554 is a non-R-loop-forming genomic locus (HGNC:26629) serving as a negative control; while MYADM is a strong R loop-forming locus (HGNC: 7544) as a positive control.

Example 3—Results

Figure 1B:
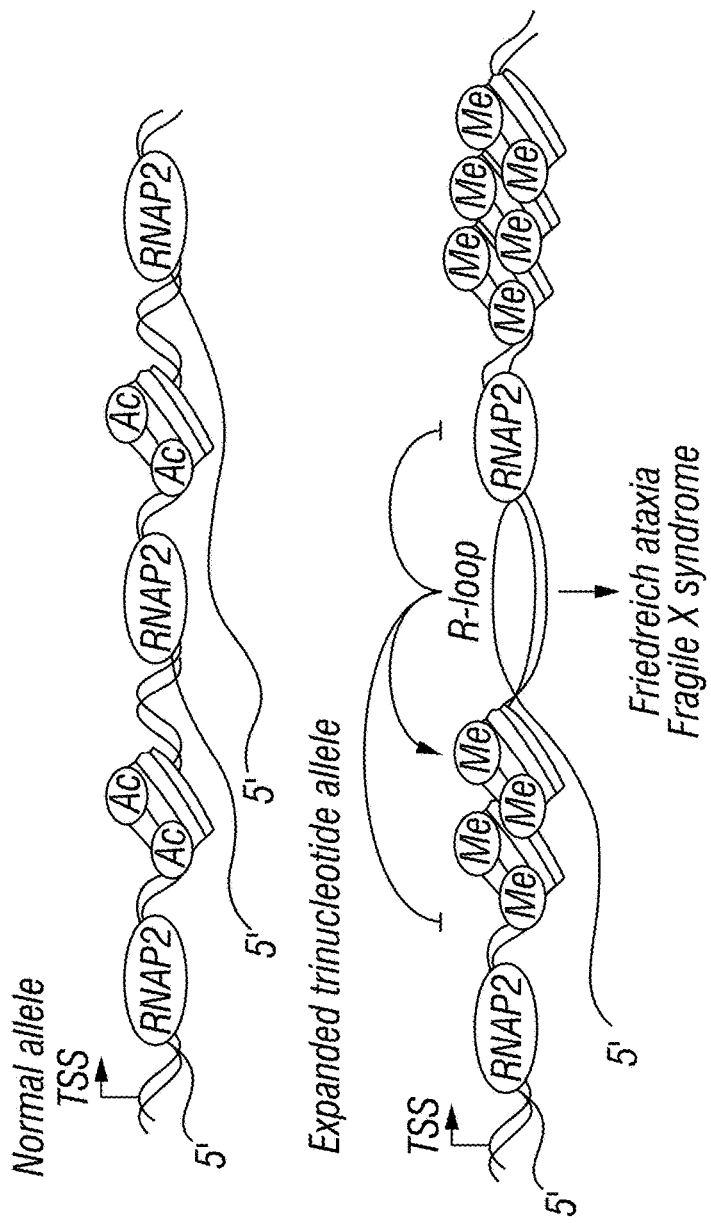

Design of anti-GAA Duplex RNAs. The inventors designed duplex RNAs complementary to the GAA repeat within FXN pre-mRNA (FIG. 1C, Table S1). The anti-GAA RNAs or control duplexes were transfected into GM03816 patient-derived fibroblast cells using cationic lipid. Three different anti-GAA duplexes each possessed a different register (siAAG, siAGA, siGAA) relative to the repeat target. The duplex RNAs were either fully complementary to the mutant FXN repeat or contained central mismatches. Duplex RNAs that contain central mismatches can bind to target RNAs but cannot engage the cleavage function of AGO2 (Herman et al., 2006).

Figure 6:
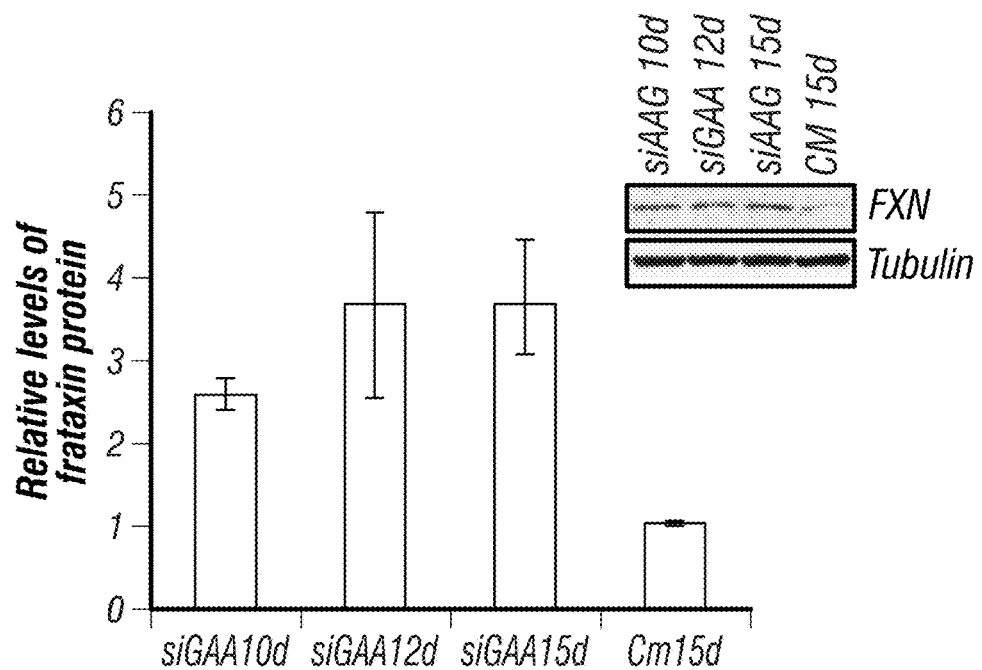
FIG. 6. Effects of anti-GAA duplex RNAs on FXN protein expression over time. FRDA patient fibroblast cells (GM03816) were treated with 50 nM of siRNAs. Data are presented as Mean±SD, n=2.
Figure 7:
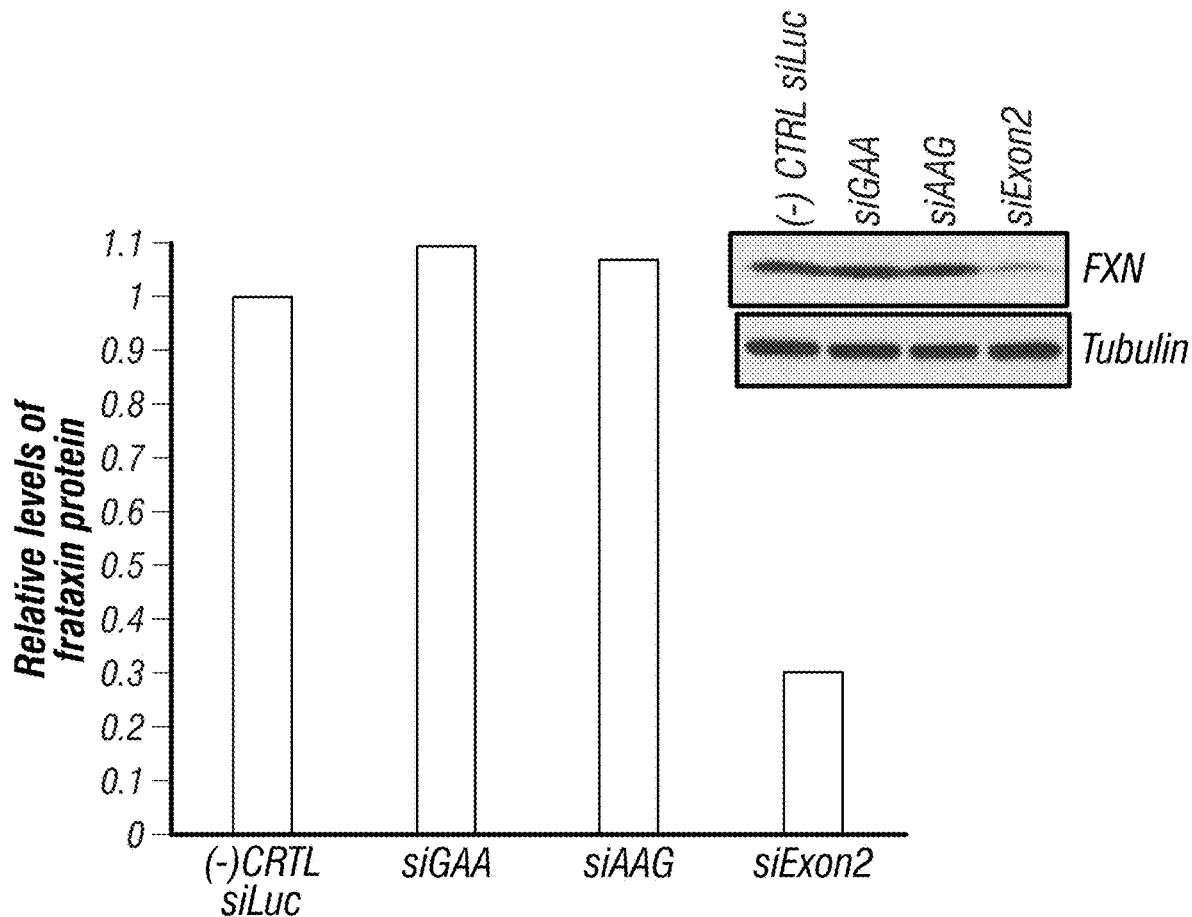
FIG. 7. Anti-GAA duplex RNAs do not influence FXN protein expression in wild-type cells. siLuc is a negative control duplex siRNA that is not complementary to FXN RNA and has no target in the genome. For the western analysis, protein sample of each treatment was collected from 3 individual transfections 4 days after transfection of wild-type fibroblast cells (GM02513) with 25 nM siRNAs.

Anti-GAA RNAs up-regulate FXN expression. The inventors introduced duplex RNAs into patient-derived GM03816 cells and observed increased expression of FXN mRNA and protein (FIGS. 1D-F, FIGS. 5A-D). Upregulation of FXN mRNA levels was 3-4 fold while protein levels were increased 4-6 fold. Half-maximal activation was achieved after addition 10-15 nM RNA (FIG. 1F). This potency is typical of that observed for other activating synthetic RNAs (Matsui et al., 2013). Activation continued to be observed fifteen days after addition of duplex RNA (FIG. 6) Addition of anti-GAA duplex RNAs did not up-regulate FXN protein expression in a fibroblast cell line, GM02513, with wild-type levels of FXN (FIG. 7).

Figure 9:
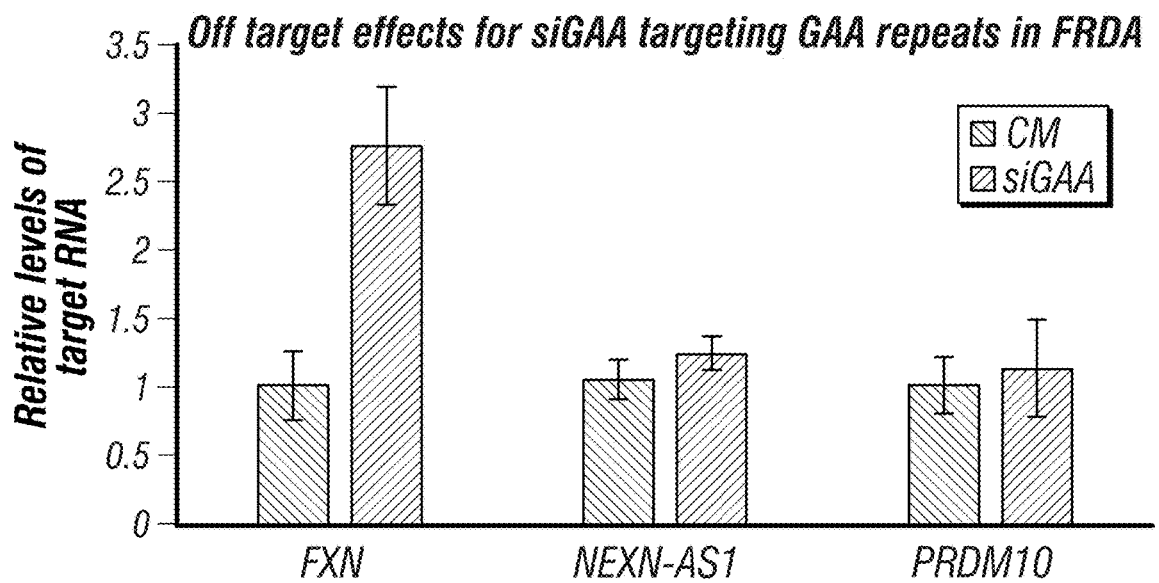
FIG. 9. Effects of anti-GAA duplex RNA on target RNA expression. FRDA patient fibroblast cells (GM03816) were treated with 50 nM of siRNAs in 15 cm plates. siGAA (right hand column of each pair) is duplex RNA complementary to the expanded repeat. CM (left hand column of each pair) is a negative control RNAs that is not complementary to FXN RNA. Data are presented as Mean±SD, n=3.

Negative control duplex RNAs containing scrambled sequences, five mismatched bases, or that had no complementarity did not activate FXN expression. One source of off-target effects by oligonucleotides is induction of interferon responsive genes, but no activation of interferon responsive genes was observed (FIG. 8). The inventors also measured expression of NEXN-AS1 and PRDM10, genes containing 32 or 10 GAA repeats respectively (FIG. 9). Expression levels of the GAA-repeat genes were unchanged.

Figure 2B:
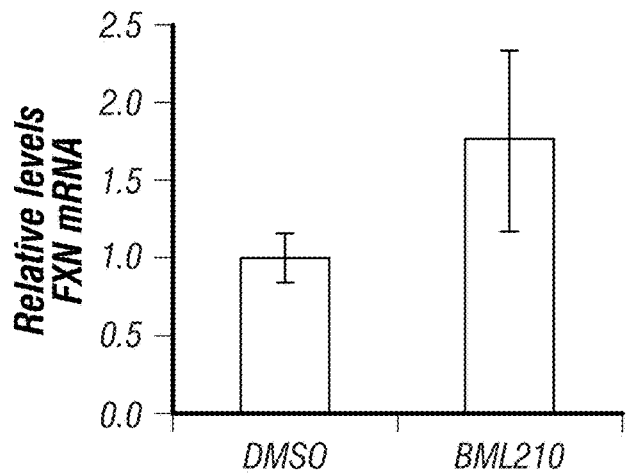
Figure 2C:
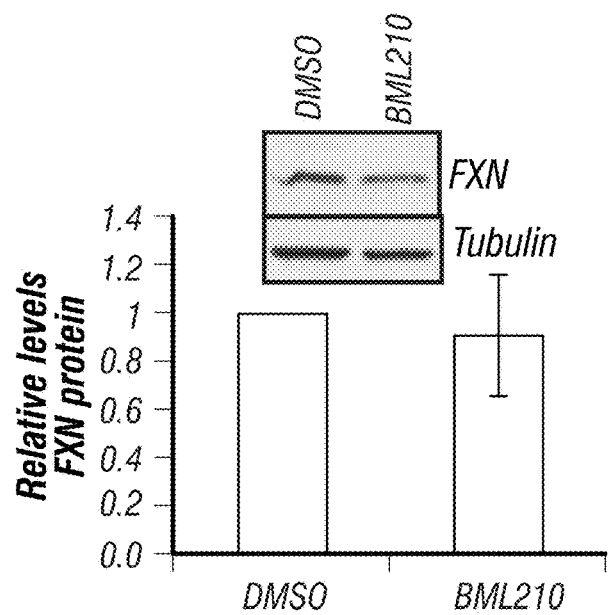

The levels of FXN protein upon addition of activating duplex RNAs were similar to the wild-type levels in GM02513 cells (FIG. 2A), suggesting that RNA-mediated upregulation can induce expression of physiologically relevant amounts of the protein. For comparison, the inventors examined levels of FXN expression in patient-derived GM03816 cells that had been treated with BML210, a small molecule known to induce histone modifications and has been reported to cause activation of FXN (Liu et al., 2004). Averaged quadruplicate experiments did not reveal a significant increase in FXN mRNA or protein levels upon treatment of GM03816 cells with BML210 (FIGS. 2B-C).

Duplex RNAs recruit AGO2 to mutant intronic GAA repeat. These activating RNAs are double-stranded and identical in design to siRNAs typically used for RNA silencing. The duplex RNAs may, therefore, be acting through the RNAi pathway in cell nuclei by binding to the expanded repeat and recruiting RNAi factors. One factor, Ago2 is the central protein component of the cellular RNAi machinery (Wang et al., 2008). Ago2 binds the guide strand of duplex RNA and participates in efficient recognition of mRNA. The inventors had previously observed that transfection of RNAs that activate progesterone receptor or cyclooxygenase-2 expression lead to binding of the Ago2 to the target transcript overlapping the gene promoters (Matsui et al., 2013).

The inventors examined recognition of the repeat-containing intronic transcript and RNA:Ago2 complex using RNA immunoprecipitation (RIP) with an anti-Ago2 antibody. They transfected cells with anti-GAA RNA, isolated RNA from cell nuclei, and purified Ago-bound RNA. Analysis of immunoprecipitated RNA by reverse transcriptase PCR (RT-PCR) revealed binding of Ago2 to FXN pre-mRNA repeat when synthetic RNA complementary to the GAA repeat was added to cells (FIG. 3A, FIG. 11). These data suggest that the first step in the mechanism of activation is RNA-mediated recruitment of Ago2 to the target transcript.

Activation does not require AGO2-mediated cleavage of FXN intronic RNA. Ago2 will cleave target mRNA if the strands have perfect complementarity at key central bases (Liu et al., 2004). If central mismatches are introduced, however, AGO2 will not cleave the target strands but will retain the ability to bind (Wang et al., 2008). This is a useful feature for investigating mechanism because it allows the potential for strand cleavage to be evaluated for its contribution to RNA-mediated control of gene expression. To determine whether cleavage of the transcript was essential for activating FXN expression, the inventors evaluated anti GAA RNA (siGAA9.10 mm) that contained mismatched bases in its central region relative to the repeat region at positions 9 and 10 (FIG. 3B). This mismatch-containing RNA activated FXN expression as well as fully complementary duplexes siGAA or siAAG, demonstrating that cleavage of the target transcript is not a necessary feature of the mechanism of action. This finding demonstrates that binding of the RNA-AGO2 complex is sufficient to trigger activation and is consistent with a mechanism of action that involves blocking association with FXN genomic DNA.

Figure 3C:
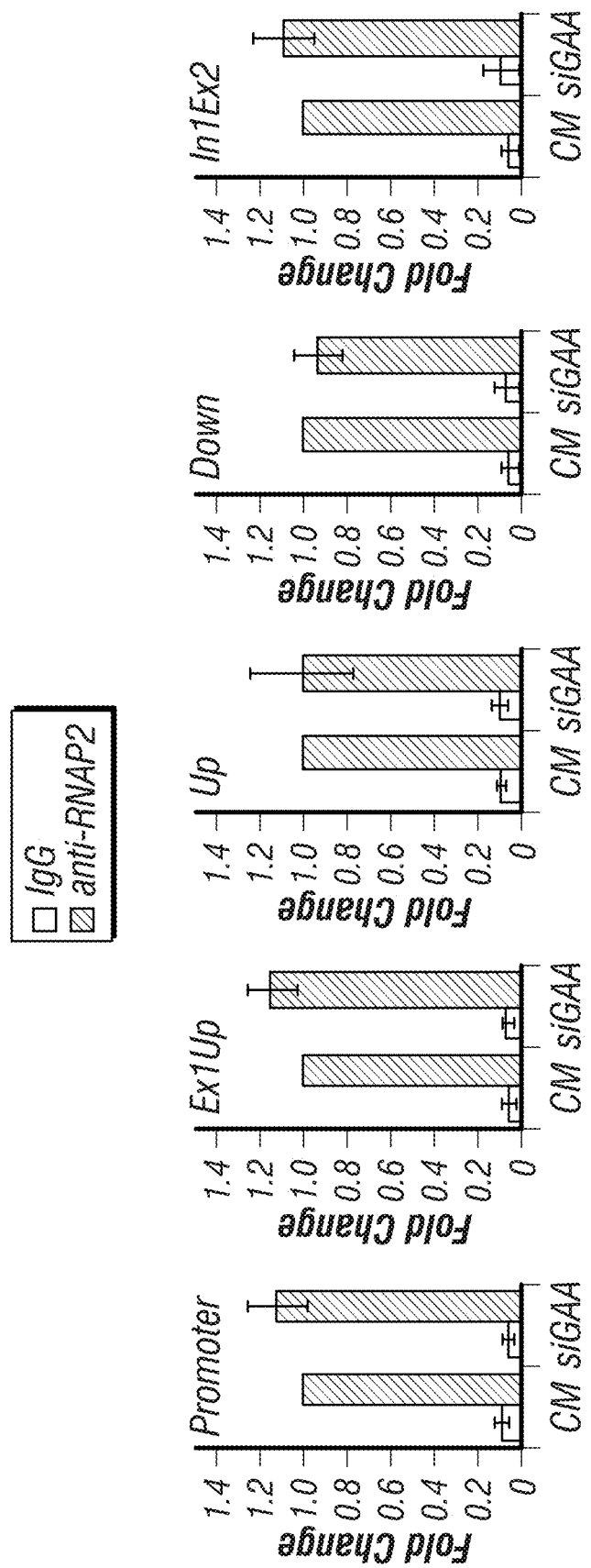

Activation is associated with activating histone modifications. The inventors performed chromatin immunoprecipitation (ChIP) for RNAP2 to investigate whether the association of RNAP2 with the FXN locus changes upon anti-GAA duplex RNA treatment. They observed no enhanced recruitment of RNAP2 at the FXN gene promoter and four regions downstream (FIG. 3C, Table S2). This finding is consistent with a previous report that there was no difference in levels of phosphorylated RNA polymerase 2 (RNAP2) between the wild-type and FRDA patient-derived lymphocytes (Punga and Buhler, 2010).

The inventors also performed ChIP to investigate how activating duplex RNA affect levels of histone modifications at the FXN gene locus. Changes of histone acetylation in the promoter and regions upstream and downstream of the GAA repeats in the first intron of FXN gene have been investigated previously (Al-Mahdawi et al. 2008; Herman et al., 2006). The studies revealed decreased levels of acetylated histone H3 and H4 (H3K9Ac, H3K14Ac, H4K5Ac, H4K8Ac, H4K12Ac, H4K16Ac) in the FRDA lymphoid cell line (GM15850) (Herman et al., 2006) or human tissues (Al-Mahdawi et al. 2008). Treatment with HDAC inhibitor BML210 increased acetylation of histone H3 and H4 leading to upregulation of FXN mRNA and protein in the lymphoid cells or primary lymphocytes (Herman et al., 2006).

Figure 3D:
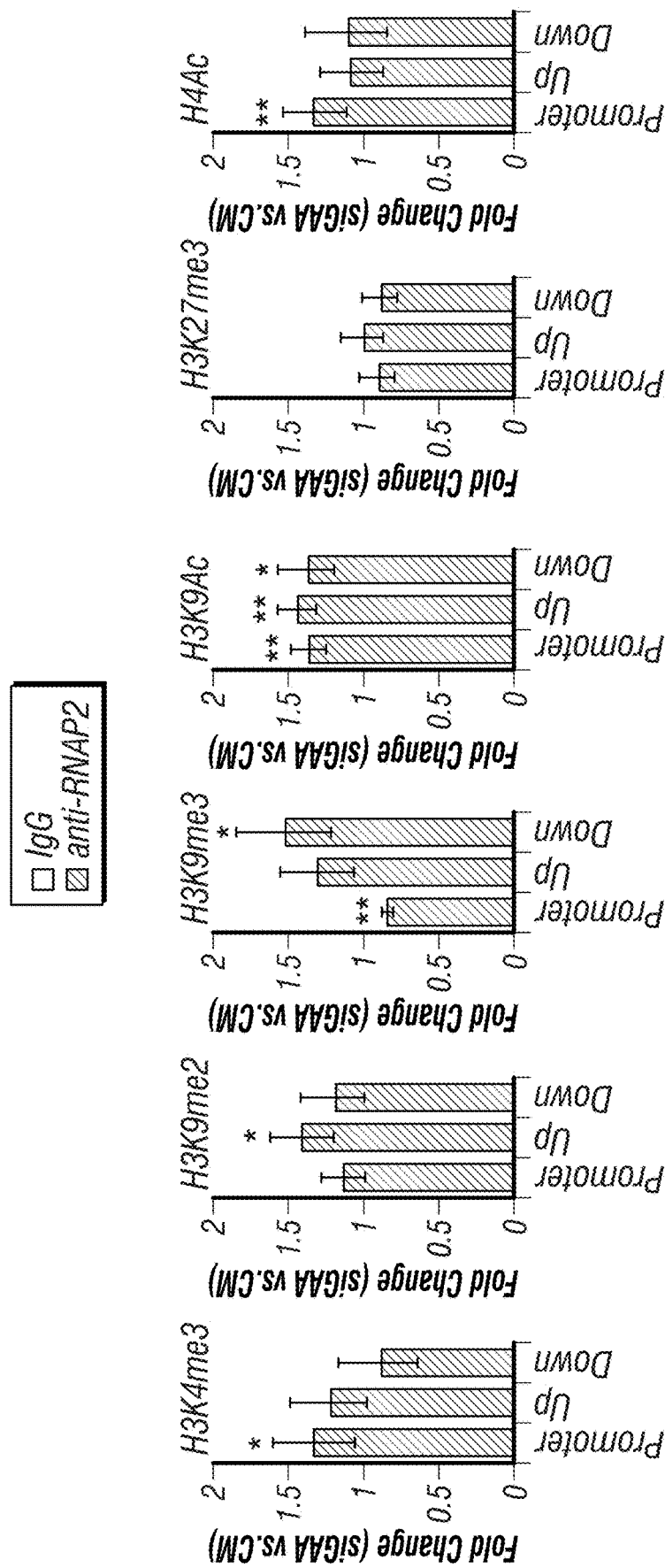

The inventor measured levels of H3K9Ac and H4Ac in the promoter and regions upstream and downstream of the GAA repeats upon control or anti-GAA duplex RNA treatment (FIG. 3D). The duplex RNA targeting the GAA repeats increased H3K9Ac levels by ~1.4-fold relative to the control duplex RNA in the promoter and upstream/downstream regions of the GAA repeats, while H4Ac levels increased by ~1.3-fold only in the promoter region. These results suggest that the activating duplex RNA can reverse histone acetylation associated with the repeat expansion and lead to activation of FXN gene.

The inventors also investigated levels of H3K4me3, H3K9me2, H3K9me3, and H3K27me3 (FIG. 3D). Previous research reported increased levels of di- and tri-methylated histone H3 correlated with DNA hypermethylation at the upstream region (Greene et al., 2007; Al-Mahdawi et al. 2008) and hypomethylation at the downstream region (Al-Mahdawi et al. 2008) of the repeats in lymphoblasts, brain, or heart tissues derived from FRDA affected individuals. Upon transfection of activating anti-GAA duplex RNA into FRDA fibroblast cells, the inventors observed increase of H3K9me2 or H3K9me3 levels (up to 1.5-fold) at the upstream and/or downstream regions of the repeats, showing that upregulation of FXN gene by duplex RNA couples with change of histone methylation. These results suggest that the duplex RNA changes status of histone methylation as well as histone acetylation at the FXN gene locus and relieve heterochromatin-mediated repression of FXN gene.

Figure 3E:
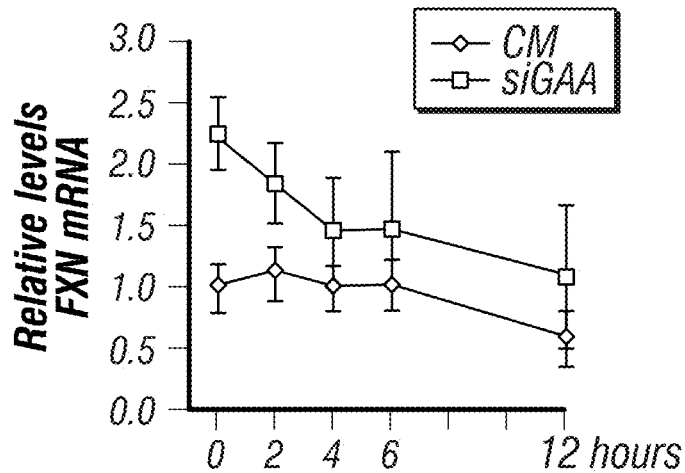

To determine whether enhanced protein stability might be involved in gene activation the inventors examined the effect of actinomycin D. Actinomycin D interferes with RNA synthesis and allows the persistence of RNA to be monitored over time. They observed that treatment with actinomycin D did not lead to stabilization of FXN RNA relative to treatment with control duplex (FIG. 3E).

These protein stability data, together with the inventors' data showing unchanged recruitment of RNAP2, suggests that RNA activation by anti-GAA duplex RNAs occurs at the level of RNA synthesis but not at the level of polymerase binding. Increased expression that is not dependent on increased recruitment of RNAP2 is consistent with previous observations of the mechanism of impaired elongation in FRDA patient-derived cells (Butler et al., 2015; Li et al., 2015; Punga Buhler, 2010). The inventors' observation of RNA-induced histone modifications is also consistent with relief of heterochromatin formation, suggesting that transcript elongation is being enhanced.

Figure 12:
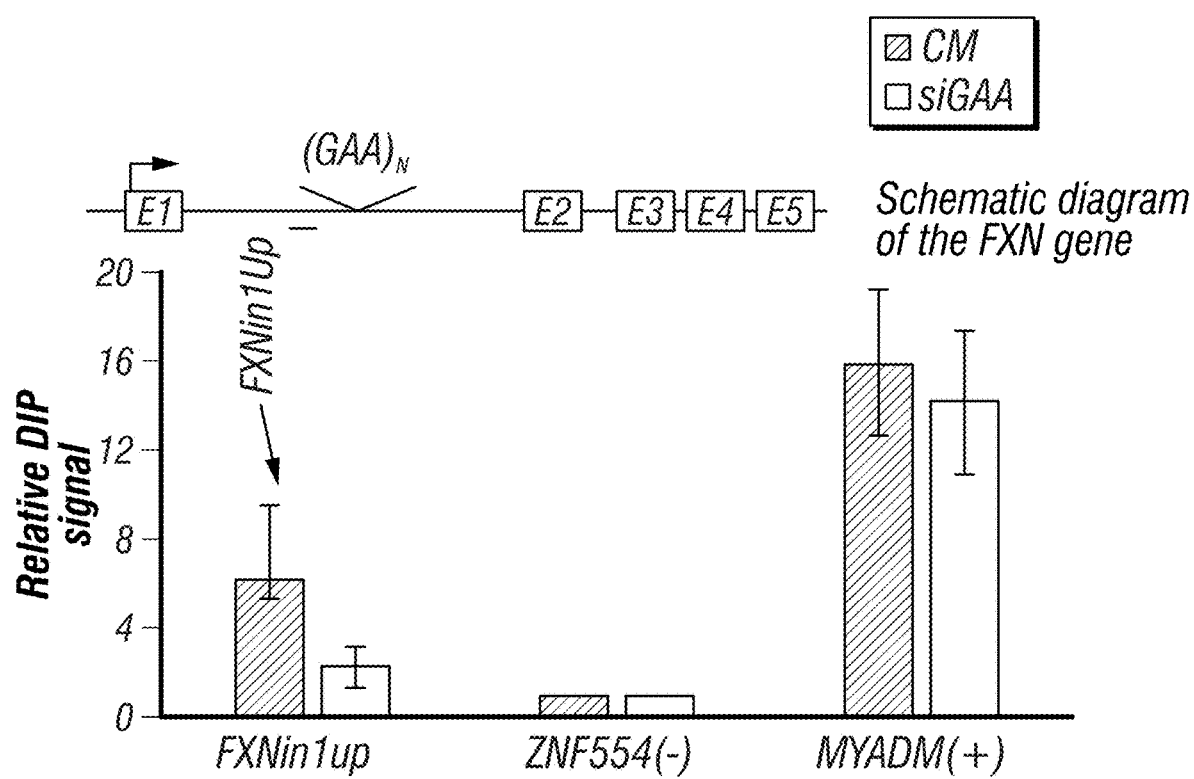
FIG. 12. Effects of anti-GAA duplex RNAs on R-oop formation at intron 1 repeat region. FRDA patient fibroblast cells (GM03816) were treated with siRNAs CM and siGAA. siGAA is duplex RNA complementary to the expanded repeat in three different registers. CM is a negative control RNAs that is not complementary to FXN RNA. DNA IP (DIP) was performed by DNA-RNA specific antibody S9.6 (Kerafast). FXNin1UP is the region adjacent to the GAA repeat region of FXN intron 1. ZNF554 is a non-R-loop-forming genomic locus (HGNC:26629) serving as a negative control; while MYADM is a strong R loop-forming locus (HGNC:7544) as a positive control (Loomis et al.,) PLoSGenet 10(4): e1004294. doi:10.1371/journal.pgen.1004294, 2014). Data are presented as Mean±SE, n=5

R-loop formation is measured by immunodetection of the RNA-DNA hybrid at a site of interest. Using this method, DNA immunoprecipitation (DIP), Gromak and colleagues have shown that R-loops promote gene silencing in Friedreich Ataxia patient-derived cells.[18] The inventors observed that addition of anti-AAG RNAs reversed R-loop formation (FIG. 12). The finding that reversed R-loop formation correlates with elevated FXN protein expression is consistent with predictions by Gromak.

Single-stranded LNA oligonucleotides also activate FXN expression. Duplex RNAs have the potential to target either sense or antisense transcripts at the FXN locus. To further define the molecular target and mechanism, the inventors tested anti-GAA locked nucleic acid (LNA) oligomers for their ability to affect FXN expression (Table S2). Single-stranded LNAs were designed to be complementary to either FXN pre-mRNA or a complementary antisense transcript, but not both, allowing the molecular target to be more accurately assessed.

Figure 4A:
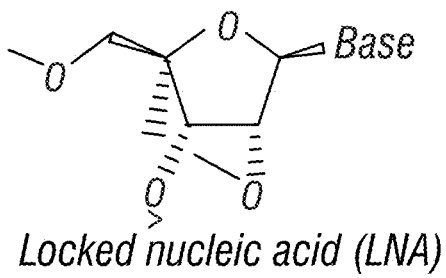
FIGS. 4A-G. LNA-mediated activation of FXN expression.
Figure 4B:
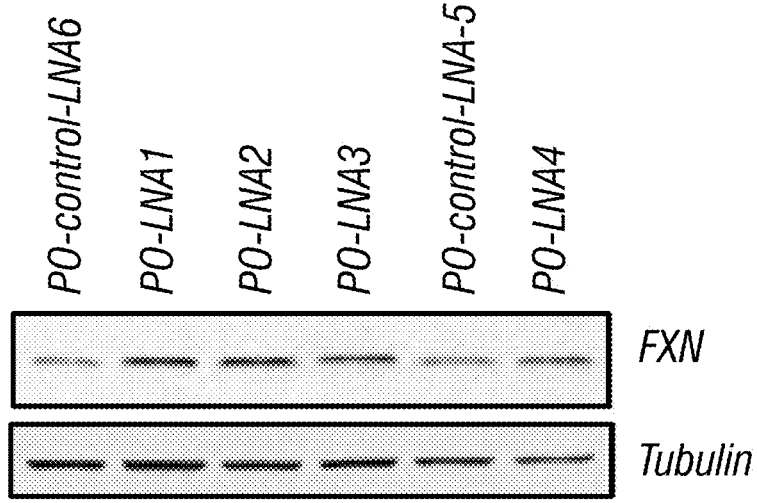
Figure 4C:
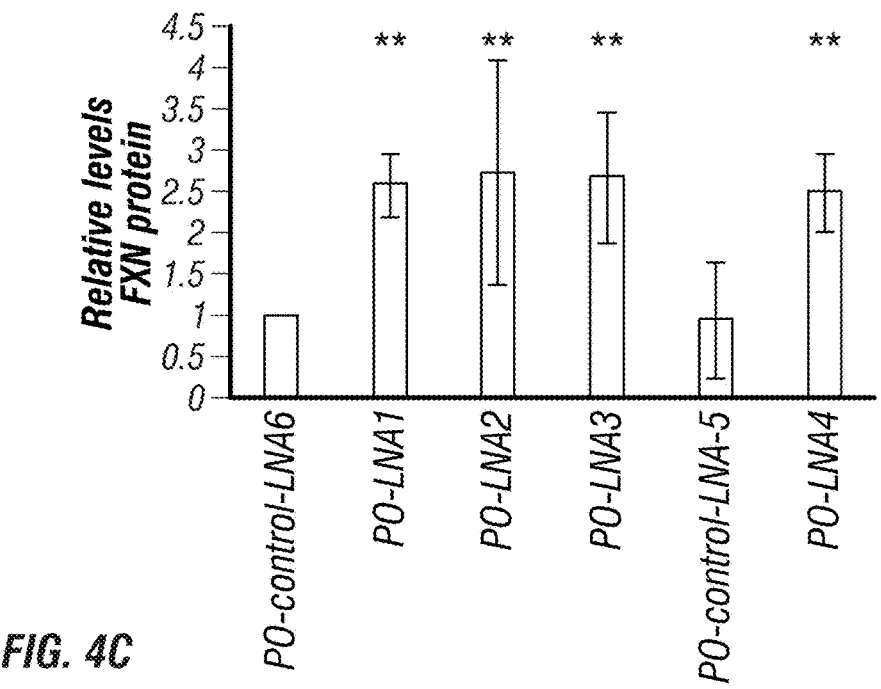
Figure 4D:
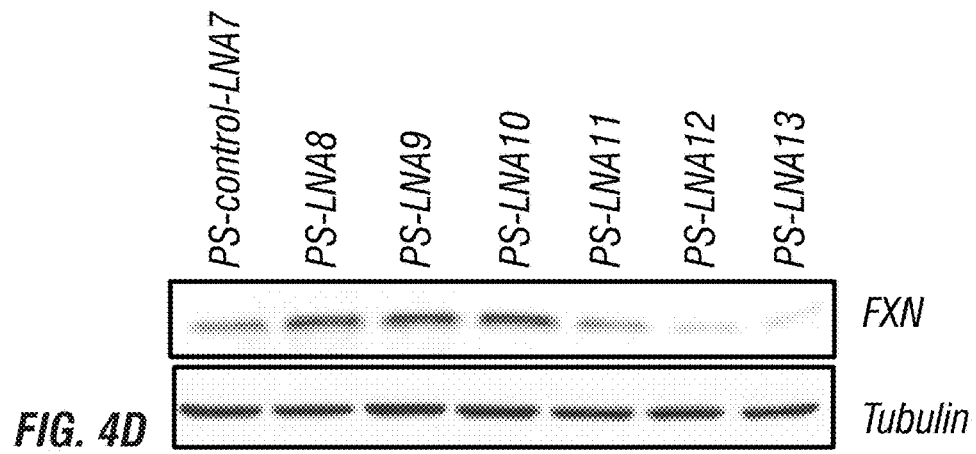
Figure 4E:
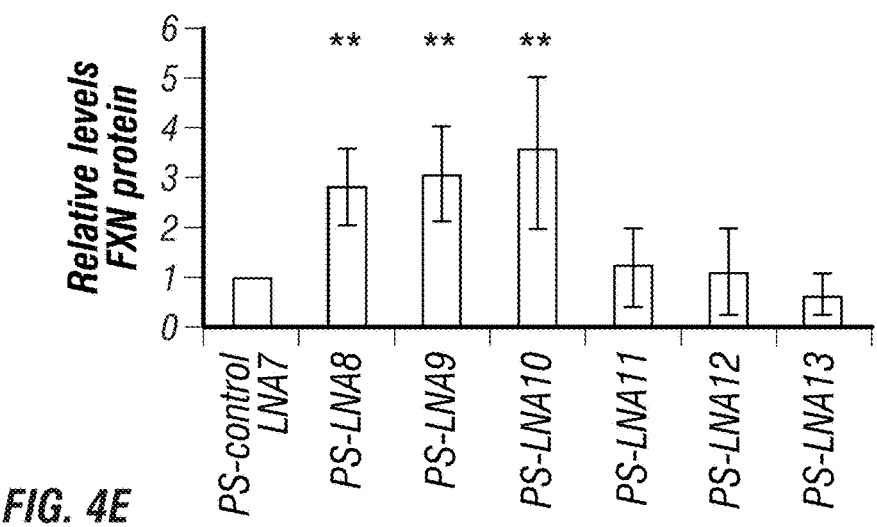
Figure 4F:
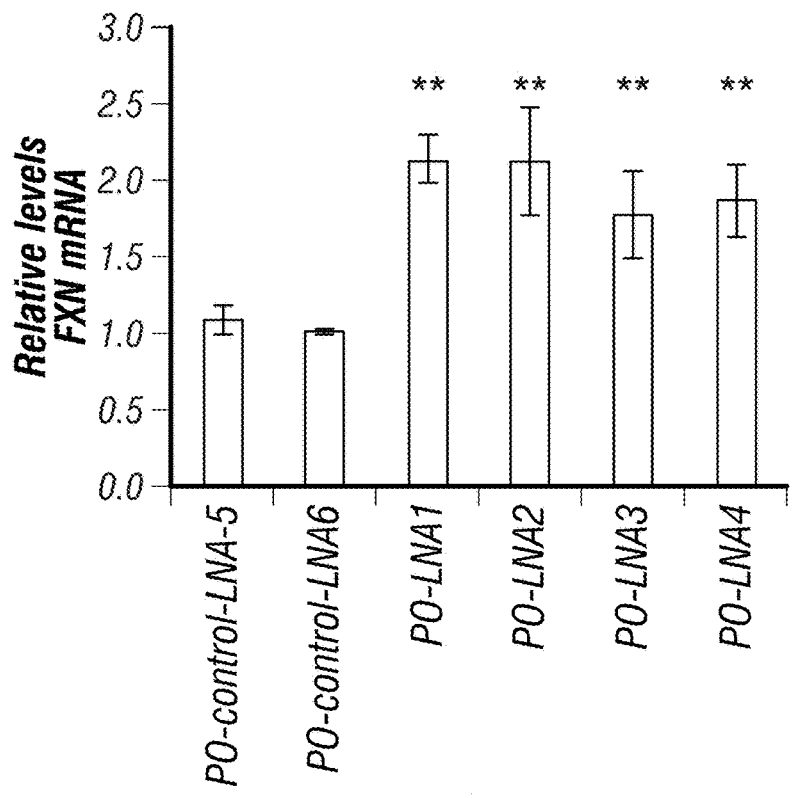
Figure 4G:
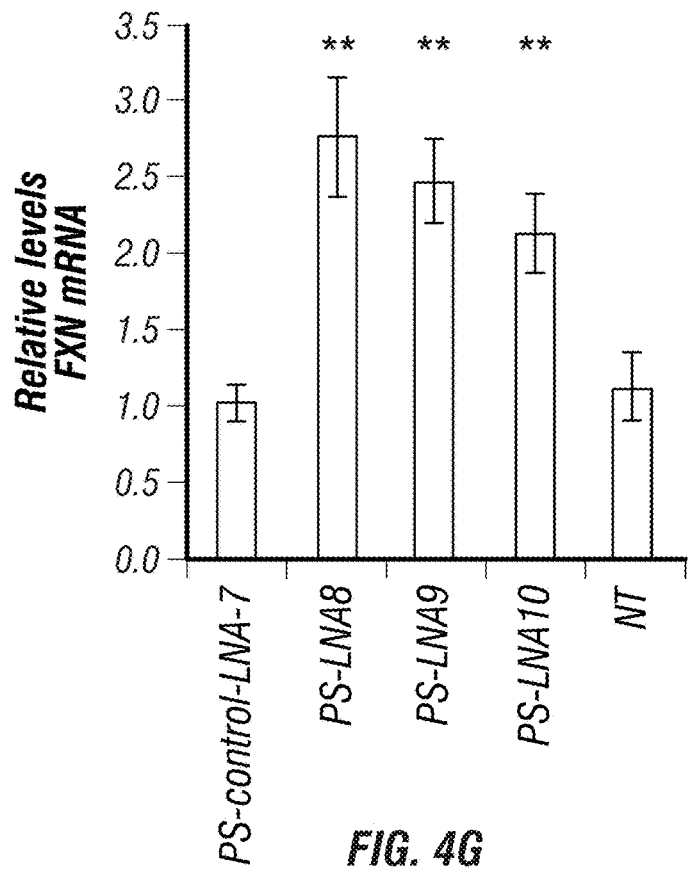
Figure 5A:
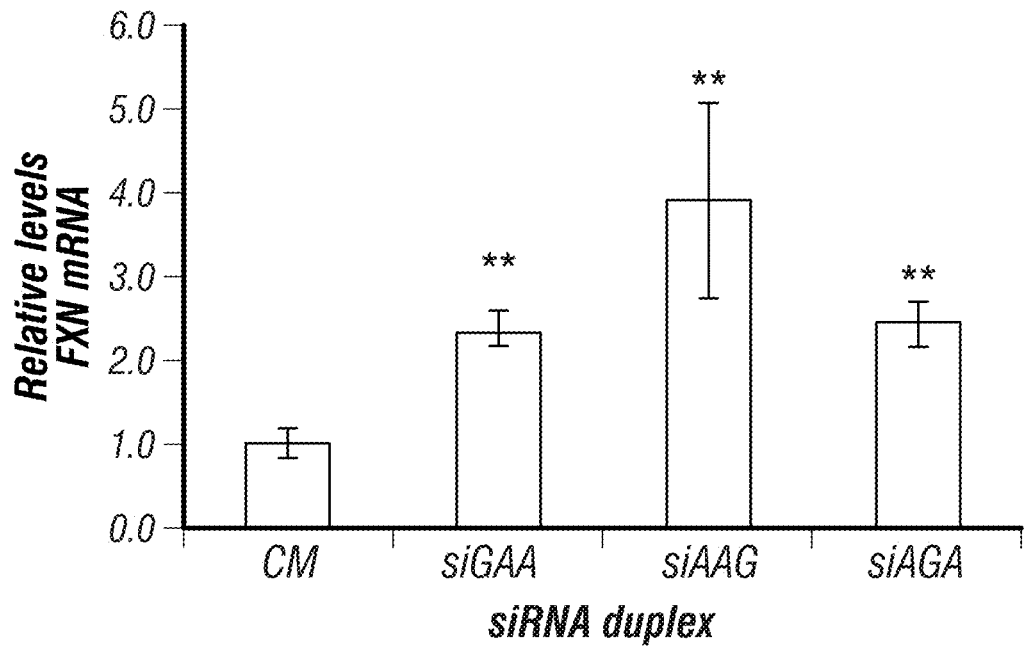
FIGS. 5A-D.
Figure 5B:
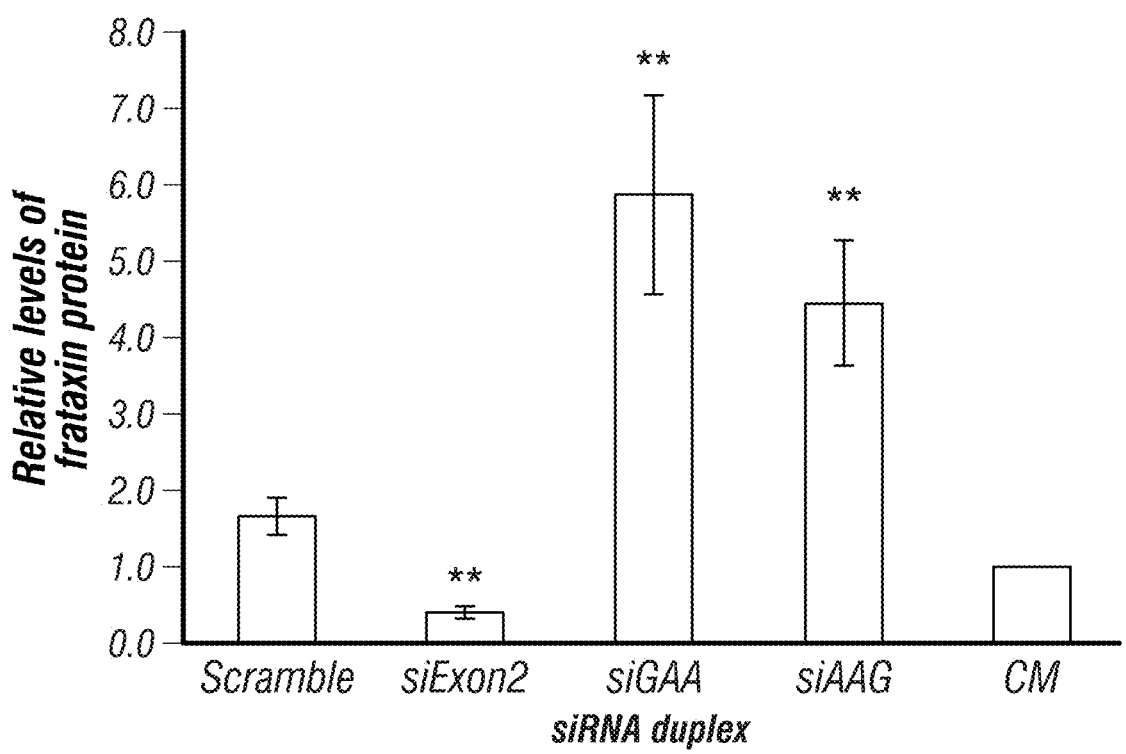
Figure 5C:
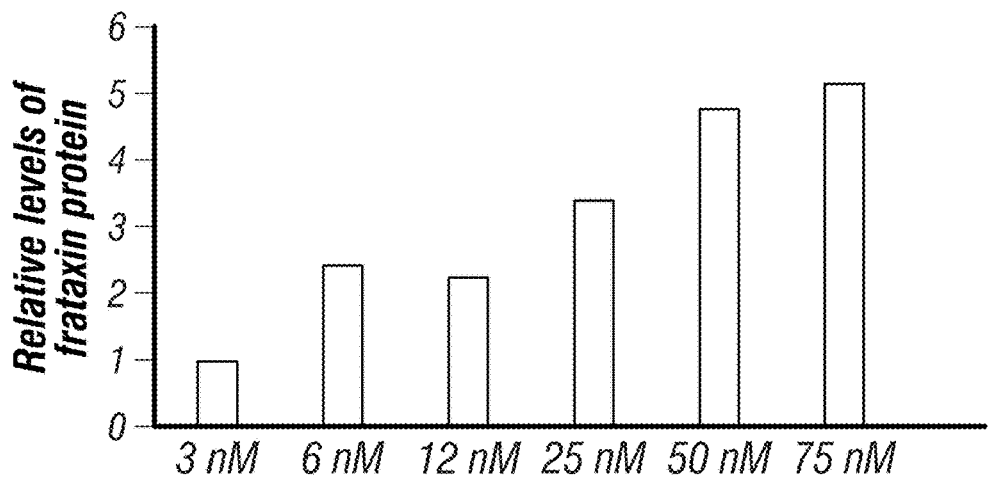
Figure 5D:
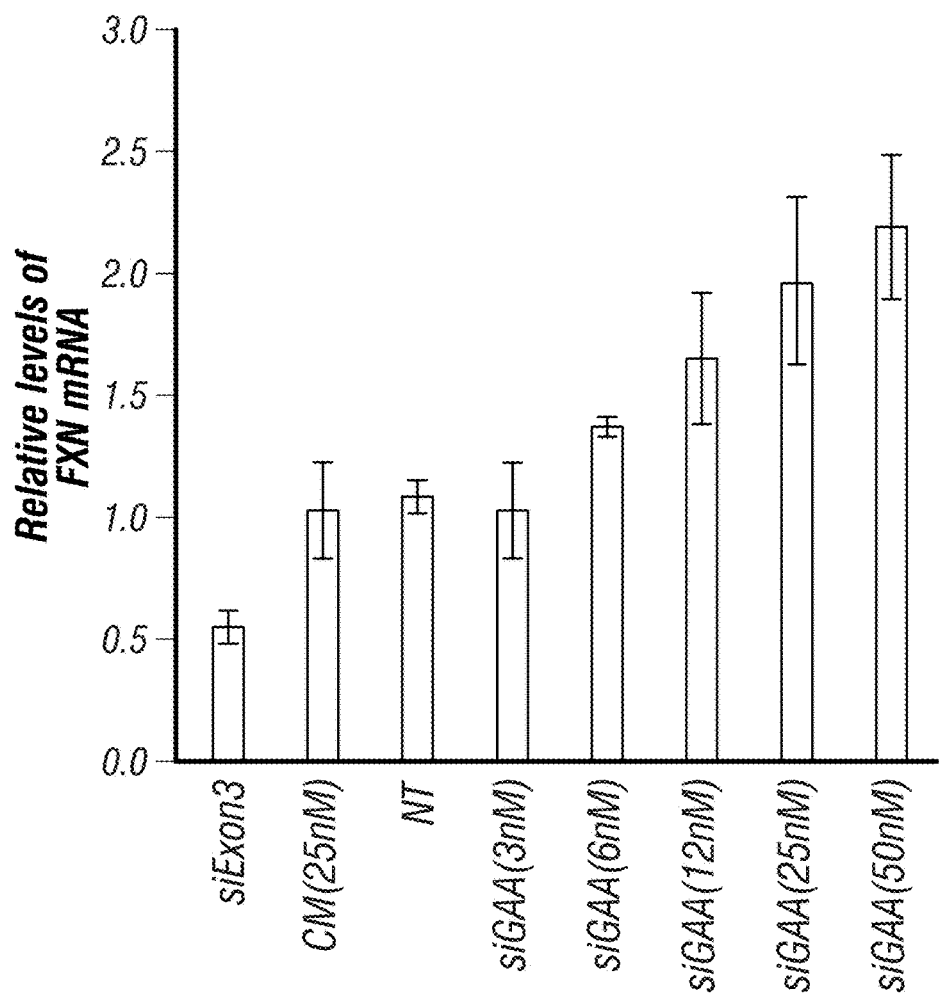

LNA is modified RNA base containing a methylene linkage between the 2' and 4' positions of the ribose (FIG. 4A) (Campbell & Wengel, 2011). This constraint reduces the entropy penalty of binding and the introduction of LNA bases allows hybridization affinity to be tailored for specific applications. The inventors initially tested LNAs possessing phosphodiester internucleotide linkages but also examined LNAs containing phosphorothioate linkages likely to possess better activities in vivo. They observed that anti-GAA phosphodiester and phosphorothioate LNAs increased levels of FXN protein and RNA expression (FIGS. 4B-E). By contrast, LNAs complementary to all three registers of antisense RNA (PS-LNA11, PS-LNA12, PS-LNA13) at the FXN locus were inert (FIG. 4D-E). Both phosphodiester and phosphorothioate anti-GAA LNAs also activated expression of FXN mRNA expression (FIGS. 4D-E). These findings are also consistent with a mechanism involving the LNA blocking the mutant transcript and preventing interactions that up-regulate gene expression. Since LNAs do not function through RNAi their activity supports that conclusion that simple binding to transcript is sufficient for activation.

TABLE S1 siRNAs targeting the FXN locus.

| RNA duplex | Strand | Sequence | Tm for duplex, +C | | | |
|---|---|---|---|---|---|---|
| siGAA | ss | GAAGAAGAAGAAGAAGAAGdTdT | 65.64 | SEQ ID NO: | 1 |
| | as | CUUCUUCUUCUUCUUCUUCdTdT | | SEQ ID NO: | 9 |
| siAAG | ss | AAGAAGAAGAAGAAGAAGAdTdT | 64.67 | SEQ ID NO: | 2 |
| | as | UCUUCUUCUUCUUCUUCUUdTdT | | SEQ ID NO: | 10 |
| siAGA | ss | AGAAGAAGAAGAAGAAGAAdTdT | 64.3 | SEQ ID NO: | 11 |
| | as | UUCUUCUUCUUCUUCUUCUdTdT | | SEQ ID NO: | 12 |
| siExon2 | ss | GAGUGUCUAUUUGAUGAAUdTdT | 64.53 | SEQ ID NO: | 13 |
| | as | AUUCAUCAAAUAGACACUCdTdT | | SEQ ID NO: | 14 |
| scramble | ss | GAGAAAGAGAAAAGGAAAGdTdT | 66.13 | SEQ ID NO: | 15 |
| | as | CUUUCCUUUUCUCUUUCUCdTdT | | SEQ ID NO: | 16 |
| siAAG5mm | ss | AACAATAATACGCAGAAGAdTdT | 63.24 | SEQ ID NO: | 17 |
| | as | UCUUCUGCGUAUUAUUGUUdTdT | | SEQ ID NO: | 18 |
| siGAA9,10mm | ss | GAAGAAGAUCAAGAAGAAGdTdT | 54.4 | SEQ ID NO: | 19 |
| | as | CUUCUUCUUAGUCUUCUUCdTdT | | SEQ ID NO: | 20 |

TABLE S1-continued siRNAs targeting the FXN locus.

| RNA duplex | Strand | Sequence | Tm for duplex, °C | |
|---|---|---|---|---|
| siExon3 | ss | GACCACCUAUGAAAGACUAdTdT | 73.65 | SEQ ID NO: 21 |
| | as | UAGUCUUUCAUAGGUGGUCdTdT | | SEQ ID NO: 22 |

The individual strand is shown from 5' to 3'.
Mismatched bases are underlined, in red, and in italics.
Both strands of the duplexes containing two TT overhang.
siRNAs were tested in FRDA patient fibroblasts GM03816 unless otherwise noted.

TABLE S2

LNAs used in the Study

| LNA | Sequence (5'-3') LNA (Bold, underlined), DNA (capital) |
|---|---|
| LNA with PO backbone | |
| PO-LNA1 | CTTCTTCTTCTTCTTCTTC SEQ ID NO: 23 |
| PO-LNA2 | TCTTCTTCTTCTTCTTCTT SEQ ID NO: 24 |
| PO-LNA3 | TTCTTCTTCTTCTTCTTCT SEQ ID NO: 25 |
| PO-LNA4 | TCTTCTTCTTCTTCTTCTT SEQ ID NO: 26 |
| PO-control-LNA5 | GCTATACCAGCGTCGTCAT SEQ ID NO: 27 |
| PO-control-LNA6 | TCTTCTGCGTATTATTGTT SEQ ID NO: 28 |
| LNA with PS backbone | |
| PS-control-LNA7 | GCTATACCAGCGTCGTCAT SEQ ID NO: 29 |
| PS-LNA8 | CTTCTTCTTCTTCTTCTTC SEQ ID NO: 30 |
| PS-LNA9 | TCTTCTTCTTCTTCTTCTT SEQ ID NO: 31 |
| PS-LNA10 | TTCTTCTTCTTCTTCTTCT SEQ ID NO: 32 |
| PS-LNA11 | GAAGAAGAAGAAGAAGAAG SEQ ID NO: 33 |
| PS-LNA12 | AAGAAGAAGAAGAAGAAGA SEQ ID NO: 34 |
| PS-LNA13 | AGAAGAAGAAGAAGAAGAA SEQ ID NO: 35 |

TABLE S3 qPCR primers for FXN locus

| Name | Sequence | Reference |
|---|---|---|
| FXNF | aagccatacacgtttgaggacta SEQ ID NO: 36 | 35 |
| FXNR | ttggcgtctgcttgttgatca SEQ ID NO: 37 | |
| Promote rF | ccccacatacccaactgctg SEQ ID NO: 38 | 36 |
| Promote rR | gcccgccgcttctaaaattc SEQ ID NO: 39 | |
| Ex1UpF | aagcaggctctccattttg SEQ ID NO: 40 | 36 |
| Ex1UpR | ccgcaggcactcttctgt SEQ ID NO: 41 | |
| In1_UpF | atggctgtggggatgaggaagat SEQ ID NO: 42 | 36 |
| In1_UpR | tgcccagacggttccctcctc SEQ ID NO: 43 | |
| In1_DownF | gcatctctggaaaaataggcaagtgt SEQ ID NO: 44 | 36 |
| In1_DownR | caggggtggaagcccaatacg SEQ ID NO: 45 | |
| In1Ex2F | agcactcggttacaggcact SEQ ID NO: 46 | 36 |
| In1Ex2R | gcccaaagttccagatttcc SEQ ID NO: 47 | |
| HsHprt1F | agttctgtggccatctgcttagtag SEQ ID NO: 48 | 35 |
| HsHprt1R | aaacaacaatccgcccaaagg SEQ ID NO: 49 | |

Example 4—Discussion

Nucleic acid therapeutics are gaining momentum as an approach to drug development (Watts & Corey, 2012). A duplex RNA for treating Transthyretin-mediated amyloidosis is now in Phase III trials (Coelho et al., 2013) and other duplex RNAs have been used successfully in primates to inhibit expression of disease genes in the central nervous system (Sah & Aronin, 2011). This recent clinical and preclinical progress suggests that using RNA to enhance FXN expression is a plausible approach for developing treatments for Friedreich's Ataxia. LNAs are also being tested in clinical trials (Watts & Corey, 2012) and provide an alternative to duplex RNAs for developing nucleic acids as therapeutic activators of FXN expression.

There is an urgent need to identify better approaches to treat Friedreich's Ataxia. This study identifies duplex RNAs and LNAs that activate FXN expression. These two distinct synthetic agents share at a common mechanistic feature—an ability to block the GAA repeat within FXN pre-mRNA. Activating RNAs and LNAs support involvement of the mutant transcript in repression of FXN expression, will be useful tools for further probing mechanism, and provide a starting point for molecular therapeutic discovery.

The molecular basis of reduced mutant FXN protein expression has been a puzzle. How can a mutation within an intron affect expression of protein derived from mature mRNA? The defect and its consequences seem at odds from the normal dogma that the direction of gene expression moves linearly from DNA to RNA to protein. In this case, an aberrant RNA seems to be affecting its own transcription.

Gromak and colleagues have provided experimental evidence for an elegant solution to this problem by demonstrating that the expanded repeat forms an R-loop with complementary DNA sequence at the FXN locus (Groh et al., 2014a; 2014b). While the inventors' activating DNAs and RNAs are therapeutic leads, they also represent mechanistic probes that independently support the conclusion that formation of an R-loop is the critical step in shutting down expression of mutant FXN. R-loops induce repressive chromatin marks at many mammalian genes (Skourti-Stathaki et al., 2014) and blocking R-loop formation may be a general strategy for controlling gene expression.

Off-target effects are an obstacle for development of nucleic acid therapeutics. The inventors do not completely examine the potential for off-target effects in this study except to demonstrate that the inventors do not observe activation of interferon responsive genes (FIG. 8) and that expression of two of the most prominent GAA-repeat containing genes is unchanged (FIG. 9). In the future, if unacceptable off-target effects are observed, they can be mitigated by changing the position of base substitutions within the anti-GAA duplex or by introducing chemically modified bases. The inventors note that a similar development strategy yielded RNAi-active single-stranded silencing anti-CAG RNAs that were potent allele-selective silencing agents and well tolerated in a mouse model for Huntington Disease[36].

Duplex RNAs and LNAs recognize complementary sequences by different mechanisms. Duplex RNAs function through the RNAi pathway. LNAs do not require the assistance of specific proteins. Both duplex RNAs and LNAs, however, form Watson-Crick hybrids that block complementary sequences and prevent R-loop formation with genomic DNA. For LNAs, only compounds complementary to sense strand FXN RNA are active, further supporting the hypothesis that the expanded mutant repeat is the key target.

The inventors' work complements the development of histone deacetylase inhibitors as a strategy for activating frataxin expression. Histone deacetylase inhibitors have the advantage of being more similar to traditional small molecule drugs, simplifying some aspects of development and clinical testing and possibly reducing barriers to delivery to target tissues in vivo. The advantage of nucleic acids is the potential for specific recognition at the FXN locus. In the future it might prove interesting to test the potential for the two strategies to function synergistically.

Finally, the ability of mammalian RNAi factors to be present and functional in cell nuclei has been open to debate. Recent evidence, however, has shown that RNAi factors exist in mammalian nuclei (Gagnon et al., 2014; Sah & Aronin, 2011; Skourti-Stathaki et al., 2014; Yu et al., 2012; Chu et al., 2010; Liu et al., 2012) and can be active controlling splicing (Chu et al., 2010; Allo et al., 2009) or transcription (Weinberg et al., 2013; Matsui et al., 2013; Morris et al. 2004; Li et al., 2006; Guo et al., 2014). These results widen the reach of nuclear RNAi by suggesting that it can be used to target intronic RNAi, interfere with R-loop formation, and release the brake on transcription.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

X. REFERENCES

The following references, to the extent that they provide exemplary procedural or other details supplementary to those set forth herein, are specifically incorporated herein by reference.

Aiba et al., *Biochemistry* 52, 9329-9338, 2013.
Akdim et al., *Am. J. Cardiol.*, 105, 1413-1419, 2010a.
Akdim, et al. *Eur. Heart J.*, 32, 2650-9, 2011.
Akdim et al., *J. Am. Coll. Cardiol.*, 55, 1611-1618, 2010b.
Al-Mahdawi et al., *Hum. Mol. Genet.* 17, 735-746, 2008.
Allo et al., *Nat. Struc. Mol. Biol.* 16, 717-724, 2009.
Bidichandani et al., *Am. J. Hum. Genet.* 62, 111-121, 1998.
Butler & Marek, *Transcription* 6, 33-36, 2015.
Campbell & Wengel, *Chem. Soc. Rev.* 40, 5680-5689, 2011.
Chan et al., *Hum. Mol. Gen.* 22, 2662-2675, 2013.
Chu et al., *Nucleic Acids Res*, 38, 7736-7748, 2010.
Coelho et al., *N. Eng. J. Med.* 369, 819-828, 2013.
Collins, *Neurol. Clin.* 31, 1095-1120, 2013.
Gagnon et al., *Biochemistry* 49, 10166-10178, 2010.
Gagnon et al., *J. Am. Chem. Soc.* 133, 8484-8407, 2011.
Gagnon et al., *Cell Reports* 6, 211-221, 2014.
Gottesfeld et al., *J. Neurochem.* 126, 147-154, 2013.
Grabczyk et al., *Nucl. Acids Res.* 35, 5351-5359, 2007.
Greene et al., *Nucl. Acids. Res.* 35, 3383-3390, 2007.
Groh et al., *Biochem. Soc. Trans.* 42, 1123-1128, 2014b.
Groh et al., *PLOS Gen.* 10, e1004318, 2014a.
Guo et al., *RNA Biol.* 11, 1221-1225, 2014.
Herman et al., *Nat. Chem. Biol.* 2, 551-558, 2006
Hu et al., *Biochemistry* 53, 4510-4518, 2014.
Hu et al., *Chem. Biol.* 17, 1183-1188, 2010.
Hu et al., *Nat. Biotechnol.* 27, 478-484, 2009.
Hu et al., *Nucleic Acid Therapeutics* 24, 199-209, 2014.
Hu et al., *Nucleic Acids Res.* 40, 11270-11280, 2012.
Kumari, et al., *Bioch. Biophys. Acta* 1819, 802-810, 2012.
Libri et al., *Lancet* 384, 504-513, 2014.
Lima et al., *Cell* 150, 883-894, 2012.
Liu et al., *Nucleic Acids Res.* 41, 9570-9583, 2013.
Li et al., *Proc. Natl. Acad. Sci. USA* 103, 17337-17342, 2006.
Li et al., *Hum. Mol. Gen.*, 24, 6932-43, 2015.
Liu et al., *Science* 305, 1437-1441, 2004.
Liu et al., *Nucleic Acids Research*, 40, 1240-1250, 2012.
Loomis et al., *PLoS Genet* 10, e1004294. doi:10.1371/journal.pgen.1004294, 2014.
Marmolino, *Brain Res. Rev.* 67, 311-330, 2011.

Matsui and Corey, *Drug Discov. Today* 17, 443-450, 2012.
Matsui et al., *Chem. Biol.* 17, 1344-1355, 2010.
Matsui et al., *Nucleic Acids Res.* 41, 10086-10109. NAR Breakthrough Article, 2013.
Miller et al., *Lancet Neurol.* 12, 435-442, 2013.
Ohshima et al., *J. Biol. Chem.* 273, 14588-14595, 1998.
Pandolfo, *J. Neurol.* 256, 3-8, 2009.
Passini et al., *Science Trans. Med.* 3, 1-11, 2011.
PCT International Applications Nos. PCT/US2008/066154.
PCT International Applications Nos. PCT/US2008/068922.
PCT International Applications Nos. PCT/US2008/064591.
Punga and Buhler, *EMBO Mol. Med.* 2, 120-129, 2010.
Querbes et al., *Oligonucleotides* 19, 23-29, 2008.
Richardson et al., *Brain Res.* 1514, 91-97, 2013.
Robinson, *J. Manag. Care Pharm.,* 19, 139-149, 2013.
Sah & Aronin, *J. Clin. Invest.* 121, 500-507, 2011.
Sahdeo et al., *Hum. Mol. Gen.,* 23, 6848-62 2014.
Sandi et al., *Neurobiol. Dis.* 42, 496-505, 2011.
Schwartz, et al., *Nat. Struct. Mol. Biol.* 15, 842-848, 2008.
Skourti-Stathaki et al., *Nature* 516, 436-439, 2014.
Smith et al., *J. Clin. Invest.* 116, 2290-2296, 2006.
Soragni et al., *Annals Neurol.,* 76, 489-508, 2014.
Szoka and Papahadjopoulos, *Proc Natl Acad Sci USA,* September; 75(9):4194-8, 1978.
Trudgian et al., *Proteomics* 11, 2790-2797, 2011.
U.S. Pat. No. 3,687,808
U.S. Pat. No. 4,587,044
U.S. Pat. No. 4,605,735
U.S. Pat. No. 4,667,025
U.S. Pat. No. 4,762,779
U.S. Pat. No. 4,789,737
U.S. Pat. No. 4,824,941
U.S. Pat. No. 4,828,979
U.S. Pat. No. 4,835,263
U.S. Pat. No. 4,845,205
U.S. Pat. No. 4,876,335
U.S. Pat. No. 4,904,582
U.S. Pat. No. 4,948,882
U.S. Pat. No. 4,958,013
U.S. Pat. No. 5,082,830
U.S. Pat. No. 5,082,830
U.S. Pat. No. 5,109,124
U.S. Pat. No. 5,112,963
U.S. Pat. No. 5,112,963
U.S. Pat. No. 5,118,802
U.S. Pat. No. 5,130,302
U.S. Pat. No. 5,134,066
U.S. Pat. No. 5,138,045
U.S. Pat. No. 5,175,273
U.S. Pat. No. 5,214,136
U.S. Pat. No. 5,214,136
U.S. Pat. No. 5,218,105
U.S. Pat. No. 5,245,022
U.S. Pat. No. 5,254,469
U.S. Pat. No. 5,258,506
U.S. Pat. No. 5,262,536
U.S. Pat. No. 5,272,250
U.S. Pat. No. 5,292,873
U.S. Pat. No. 5,317,098
U.S. Pat. No. 5,367,066
U.S. Pat. No. 5,371,241
U.S. Pat. No. 5,391,723
U.S. Pat. No. 5,414,077
U.S. Pat. No. 5,416,203
U.S. Pat. No. 5,432,272
U.S. Pat. No. 5,451,463
U.S. Pat. No. 5,457,187
U.S. Pat. No. 5,459,255
U.S. Pat. No. 5,484,908
U.S. Pat. No. 5,486,603
U.S. Pat. No. 5,502,177
U.S. Pat. No. 5,510,475
U.S. Pat. No. 5,512,439
U.S. Pat. No. 5,512,667
U.S. Pat. No. 5,514,785
U.S. Pat. No. 5,525,465
U.S. Pat. No. 5,525,711
U.S. Pat. No. 5,541,313
U.S. Pat. No. 5,545,730
U.S. Pat. No. 5,552,538
U.S. Pat. No. 5,552,540
U.S. Pat. No. 5,565,552
U.S. Pat. No. 5,567,810
U.S. Pat. No. 5,574,142
U.S. Pat. No. 5,578,717
U.S. Pat. No. 5,578,718
U.S. Pat. No. 5,580,731
U.S. Pat. No. 5,580,731
U.S. Pat. No. 5,585,481
U.S. Pat. No. 5,587,371
U.S. Pat. No. 5,587,469
U.S. Pat. No. 5,591,584
U.S. Pat. No. 5,594,121
U.S. Pat. No. 5,595,726
U.S. Pat. No. 5,596,091
U.S. Pat. No. 5,597,696
U.S. Pat. No. 5,599,923
U.S. Pat. No. 5,599,928
U.S. Pat. No. 5,608,046
U.S. Pat. No. 5,614,617
U.S. Pat. No. 5,645,985
U.S. Pat. No. 5,681,941
U.S. Pat. No. 5,688,941
U.S. Pat. No. 5,750,692
U.S. Pat. No. 5,763,588
U.S. Pat. No. 5,830,653
U.S. Pat. No. 6,005,096
U.S. Pat. No. 6,268,490
U.S. Pat. No. 6,525,191
U.S. Pat. No. 6,670,461
U.S. Pat. No. 6,770,748
U.S. Pat. No. 6,794,499
U.S. Pat. No. 7,034,133
U.S. Pat. No. 7,053,207
U.S. Pat. No. 7,399,845
U.S. Patent Publication No. US2007/0287831.
U.S. Patent Publication No. US2008/0039618.
U.S. Patent Publication No. US2005/0130923.
U.S. Patent Publication No. US2004/0171570.
U.S. Ser. No. 12/129,154.
U.S. Ser. No. 60/989,574.
U.S. Ser. No. 61/026,995.
U.S. Ser. No. 61/026,998.
U.S. Ser. No. 61/056,564.
U.S. Ser. No. 61/086,231.
U.S. Ser. No. 61/097,787.
U.S. Ser. No. 61/099,844.
Udd and Krahe, *Lancet* Neurol. 11, 891-905, 2012.
Wang, et al., *Nature* 456, 921-926, 2008.
Watts and Corey, *J. Pathol.* 226, 365-379, 2012.
Weinberg and Morris, *Nucleic Acid Ther.* 23, 9-14, 2013.
Yu et al., *Cell* 150, 895-908, 2012.
WO 1994/14226.
WO 2004/106356.
WO 2005/021570.
WO 2007/134181.

What is claimed:

1. A method of selectively increasing the expression of a Frataxin transcript, the method comprising delivering to a cell having a Frataxin transcript comprising an expanded GAA repeat region a double-stranded oligonucleotide, wherein the double-stranded oligonucleotide has a length of from 13 nucleobases to 22 nucleobases and comprises a repeating tri-nucleobase sequence comprising (i) GAA or CUU, (ii) AAG or UUC, or (iii) AGA or UCU.

2. The method of claim 1, wherein the expanded GAA repeat region contains 60 or more repeats.

3. The method of claim 1, wherein the expanded GAA repeat region contains from 66 to 1700 repeats.

4. The method of claim 1, wherein the cell is present in a subject having Friedreich's Ataxia.

5. The method of claim 1, wherein the double-stranded oligonucleotide has a length of from 18 to 22 nucleobases.

6. The method of claim 1, wherein the double-stranded oligonucleotide comprises RNA nucleobases.

7. The method of claim 1, wherein the double-stranded oligonucleotide comprises one or more mismatches to the target sequence.

8. The method of claim 1, wherein said delivering comprises direct administration into the central nervous system, cerebrospinal fluid, or mediated uptake across a blood brain barrier.

9. A method of treating Friedreich's Ataxia in an individual, the method comprising selectively increasing the expression of a Frataxin transcript in a cell in the individual, wherein the Frataxin transcript comprises an expanded GAA repeat region, wherein the cell is modified to comprise a double-stranded oligonucleotide, wherein the double-stranded oligonucleotide has a length of from 13 nucleobases to 22 nucleobases and comprises a repeating tri-nucleobase sequence comprising (i) GAA or CUU, (ii) AAG or UUC, or (iii) AGA or UCU, and wherein said modification increases the expression of the Frataxin transcript and treats Friedreich's Ataxia in the individual.

10. The method of claim 9, wherein the expanded GAA repeat region contains 60 or more repeats.

11. The method of claim 9, wherein the expanded GAA repeat region contains from 66 to 1700 repeats.

12. The method of claim 9, wherein the double-stranded oligonucleotide has a length of from 18 to 22 nucleobases.

13. The method of claim 9, wherein the double-stranded oligonucleotide comprises RNA nucleobases.

14. The method of claim 9, wherein the double-stranded oligonucleotide comprises one or more mismatches to the target sequence.

* * * * *

SEQUENCE LISTING

<160> NUMBER OF SEQ ID NOS: 56

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 1
gaagaagaag aagaagaagn n                                        21

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 2
aagaagaaga agaagaagan n                                        21

<210> SEQ ID NO 3
<211> LENGTH: 21
<212> TYPE: DNA
<213> ORGANISM: Artificial sequence
<220> FEATURE:
<223> OTHER INFORMATION: Synthetic primer

<400> SEQUENCE: 3
gaaacccaaa gaatggctgt g                                        21

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
ttccctcctc gtgaaacacc                                          20

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
cggggaaaag ccctataaat                                          20

```
<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
tccacattca ctgcattcgt                                           20

<210> SEQ ID NO 7
<211> LENGTH: 20
<212> TYPE: DNA
<213> ORGANISM: Artificial sequence
<220> FEATURE:
<223> OTHER INFORMATION: Synthetic primer

<400> SEQUENCE: 7
cgtaggtgcc ctagttggag                                           20

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
tccattctca ttcccaaacc                                           20

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 9
cuucuucuuc uucuucuucn n                                         21

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 10
ucuucuucuu cuucuucuun n                                         21

<210> SEQ ID NO 11
<211> LENGTH: 21
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 11
agaagaagaa gaagaagaan n                                              21

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 12
uucuucuucu ucuucuucun n                                              21

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 13
gagugucuau uugaugaaun n                                              21

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 14
auucaucaaa uagacacucn n                                              21

<210> SEQ ID NO 15
<211> LENGTH: 21
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 15
gagaaagaga aaaggaaagn n                                              21

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 16
cuuuccuuuu cucuuucucn n                                              21

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 17
aacaataata cgcagaagan n                                              21

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 18
ucuucugcgu auuauuguun n                                              21

<210> SEQ ID NO 19
```

```
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 19
gaagaagauc aagaagaagn n                                          21

<210> SEQ ID NO 20
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine

<400> SEQUENCE: 20
cuucuucuua gucuucuucd tdt                                        23

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 21
gaccaccuau gaaagacuan n                                          21

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: n = thymidine
<220> FEATURE:
<221> NAME/KEY: misc_feature
<222> LOCATION: (20)..(21)
<223> OTHER INFORMATION: n is a, c, g, t or u

<400> SEQUENCE: 22
uagucuuuca uagguggucn n                                          21

<210> SEQ ID NO 23
<211> LENGTH: 19
<212> TYPE: DNA
<213> ORGANISM: Artificial sequence
```

```
<220> FEATURE:
<223> OTHER INFORMATION: Synthetic oligonucleotide

<400> SEQUENCE: 23
cttcttcttc ttcttcttc                                                  19

<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 24
tcttcttctt cttcttctt                                                  19

<210> SEQ ID NO 25
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 25
ttcttcttct tcttcttct                                                  19

<210> SEQ ID NO 26
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 26
tcttcttctt cttcttctt                                                  19

<210> SEQ ID NO 27
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 27
gctataccag cgtcgtcat                                                  19

<210> SEQ ID NO 28
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 28
tcttctgcgt attattgtt                                                  19

<210> SEQ ID NO 29
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 29
gctataccag cgtcgtcat                                                  19
```

```
<210> SEQ ID NO 30
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 30
cttcttcttc ttcttcttc                                                    19

<210> SEQ ID NO 31
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 31
tcttcttctt cttcttctt                                                    19

<210> SEQ ID NO 32
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 32
ttcttcttct tcttcttct                                                    19

<210> SEQ ID NO 33
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 33
gaagaagaag aagaagaag                                                    19

<210> SEQ ID NO 34
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 34
aagaagaaga agaagaaga                                                    19

<210> SEQ ID NO 35
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 35
agaagaagaa gaagaagaa                                                    19

<210> SEQ ID NO 36
<211> LENGTH: 23
<212> TYPE: DNA
<213> ORGANISM: Artificial sequence
<220> FEATURE:
<223> OTHER INFORMATION: Synthetic primer
```

```
<400> SEQUENCE: 36
aagccataca cgtttgagga cta                                          23

<210> SEQ ID NO 37
<211> LENGTH: 21
<212> TYPE: DNA
<213> ORGANISM: Artificial sequence
<220> FEATURE:
<223> OTHER INFORMATION: Synthetic primer

<400> SEQUENCE: 37
ttggcgtctg cttgttgatc a                                            21

<210> SEQ ID NO 38
<211> LENGTH: 20
<212> TYPE: DNA
<213> ORGANISM: Artificial sequence
<220> FEATURE:
<223> OTHER INFORMATION: Synthetic primer

<400> SEQUENCE: 38
ccccacatac ccaactgctg                                              20

<210> SEQ ID NO 39
<211> LENGTH: 20
<212> TYPE: DNA
<213> ORGANISM: Artificial sequence
<220> FEATURE:
<223> OTHER INFORMATION: Synthetic primer

<400> SEQUENCE: 39
gcccgccgct tctaaaattc                                              20

<210> SEQ ID NO 40
<211> LENGTH: 20
<212> TYPE: DNA
<213> ORGANISM: Artificial sequence
<220> FEATURE:
<223> OTHER INFORMATION: Synthetic primer

<400> SEQUENCE: 40
aagcaggctc tccatttttg                                              20

<210> SEQ ID NO 41
<211> LENGTH: 18
<212> TYPE: DNA
<213> ORGANISM: Artificial sequence
<220> FEATURE:
<223> OTHER INFORMATION: Synthetic primer

<400> SEQUENCE: 41
ccgcaggcac tcttctgt                                                18

<210> SEQ ID NO 42
<211> LENGTH: 23
<212> TYPE: DNA
<213> ORGANISM: Artificial sequence
<220> FEATURE:
<223> OTHER INFORMATION: Synthetic primer

<400> SEQUENCE: 42
atggctgtgg ggatgaggaa gat                                          23

<210> SEQ ID NO 43
```

```
<211> LENGTH: 21
<212> TYPE: DNA
<213> ORGANISM: Artificial sequence
<220> FEATURE:
<223> OTHER INFORMATION: Synthetic primer

<400> SEQUENCE: 43
tgcccagacg gttccctcct c                                              21

<210> SEQ ID NO 44
<211> LENGTH: 26
<212> TYPE: DNA
<213> ORGANISM: Artificial sequence
<220> FEATURE:
<223> OTHER INFORMATION: Synthetic primer

<400> SEQUENCE: 44
gcatctctgg aaaaataggc aagtgt                                         26

<210> SEQ ID NO 45
<211> LENGTH: 21
<212> TYPE: DNA
<213> ORGANISM: Artificial sequence
<220> FEATURE:
<223> OTHER INFORMATION: Synthetic primer

<400> SEQUENCE: 45
caggggtgga agcccaatac g                                              21

<210> SEQ ID NO 46
<211> LENGTH: 20
<212> TYPE: DNA
<213> ORGANISM: Artificial sequence
<220> FEATURE:
<223> OTHER INFORMATION: Synthetic primer

<400> SEQUENCE: 46
agcactcggt tacaggcact                                                20

<210> SEQ ID NO 47
<211> LENGTH: 20
<212> TYPE: DNA
<213> ORGANISM: Artificial sequence
<220> FEATURE:
<223> OTHER INFORMATION: Synthetic primer

<400> SEQUENCE: 47
gcccaaagtt ccagatttcc                                                20

<210> SEQ ID NO 48
<211> LENGTH: 25
<212> TYPE: DNA
<213> ORGANISM: Artificial sequence
<220> FEATURE:
<223> OTHER INFORMATION: Synthetic primer

<400> SEQUENCE: 48
agttctgtgg ccatctgctt agtag                                          25

<210> SEQ ID NO 49
<211> LENGTH: 21
<212> TYPE: DNA
<213> ORGANISM: Artificial sequence
<220> FEATURE:
<223> OTHER INFORMATION: Synthetic primer

<400> SEQUENCE: 49
```
aaacaacaat ccgcccaaag g                                                    21

<210> SEQ ID NO 50
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 50
ucuucuucuu cuucuucuu                                                       19

<210> SEQ ID NO 51
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 51
uucuucuucu ucuucuucu                                                       19

<210> SEQ ID NO 52
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 52
cuucuucuuc uucuucuuc                                                       19

<210> SEQ ID NO 53
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 53
gaagaagaag aagaagaaga agaagaagaa gaagaagaa                                 39

<210> SEQ ID NO 54
<211> LENGTH: 153
<212> TYPE: DNA
<213> ORGANISM: Artificial sequence
<220> FEATURE:
<223> OTHER INFORMATION: Synthetic oligonucleotide

<400> SEQUENCE: 54
tatgcattaa tgggttataa ttcactgaaa aatagtaacg tacttcttaa ctttggcttt          60
cagagttcga accaacgtgg cctcaaccag atttggaatg tcaaaaagca gagtgtctat         120
ttgatgaatt tgaggaaatc tggaactttg ggc                                      153

<210> SEQ ID NO 55
<211> LENGTH: 359
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(11)
<223> OTHER INFORMATION: n is a, c, g, t or u
<220> FEATURE:

```
<221> NAME/KEY: misc_feature
<222> LOCATION: (13)..(21)
<223> OTHER INFORMATION: n is a, c, g, t or u
<220> FEATURE:
<221> NAME/KEY: misc_feature
<222> LOCATION: (175)..(177)
<223> OTHER INFORMATION: n is a, c, g, t or u
<220> FEATURE:
<221> NAME/KEY: misc_feature
<222> LOCATION: (180)..(181)
<223> OTHER INFORMATION: n is a, c, g, t or u
<220> FEATURE:
<221> NAME/KEY: misc_feature
<222> LOCATION: (186)..(188)
<223> OTHER INFORMATION: n is a, c, g, t or u
<220> FEATURE:
<221> NAME/KEY: misc_feature
<222> LOCATION: (198)..(198)
<223> OTHER INFORMATION: n is a, c, g, t or u
<220> FEATURE:
<221> NAME/KEY: misc_feature
<222> LOCATION: (201)..(203)
<223> OTHER INFORMATION: n is a, c, g, t or u
<220> FEATURE:
<221> NAME/KEY: misc_feature
<222> LOCATION: (209)..(209)
<223> OTHER INFORMATION: n is a, c, g, t or u
<220> FEATURE:
<221> NAME/KEY: misc_feature
<222> LOCATION: (213)..(213)
<223> OTHER INFORMATION: n is a, c, g, t or u
<220> FEATURE:
<221> NAME/KEY: misc_feature
<222> LOCATION: (215)..(215)
<223> OTHER INFORMATION: n is a, c, g, t or u
<220> FEATURE:
<221> NAME/KEY: misc_feature
<222> LOCATION: (219)..(219)
<223> OTHER INFORMATION: n is a, c, g, t or u
<220> FEATURE:
<221> NAME/KEY: misc_feature
<222> LOCATION: (226)..(226)
<223> OTHER INFORMATION: n is a, c, g, t or u
<220> FEATURE:
<221> NAME/KEY: misc_feature
<222> LOCATION: (228)..(228)
<223> OTHER INFORMATION: n is a, c, g, t or u
<220> FEATURE:
<221> NAME/KEY: misc_feature
<222> LOCATION: (242)..(242)
<223> OTHER INFORMATION: n is a, c, g, t or u
<220> FEATURE:
<221> NAME/KEY: misc_feature
<222> LOCATION: (245)..(245)
<223> OTHER INFORMATION: n is a, c, g, t or u
<220> FEATURE:
<221> NAME/KEY: misc_feature
<222> LOCATION: (253)..(253)
<223> OTHER INFORMATION: n is a, c, g, t or u
<220> FEATURE:
<221> NAME/KEY: misc_feature
<222> LOCATION: (257)..(259)
<223> OTHER INFORMATION: n is a, c, g, t or u
<220> FEATURE:
<221> NAME/KEY: misc_feature
<222> LOCATION: (261)..(261)
<223> OTHER INFORMATION: n is a, c, g, t or u
<220> FEATURE:
<221> NAME/KEY: misc_feature
<222> LOCATION: (263)..(264)
<223> OTHER INFORMATION: n is a, c, g, t or u
<220> FEATURE:
<221> NAME/KEY: misc_feature
<222> LOCATION: (269)..(269)
<223> OTHER INFORMATION: n is a, c, g, t or u
<220> FEATURE:
<221> NAME/KEY: misc_feature
<222> LOCATION: (271)..(271)
<223> OTHER INFORMATION: n is a, c, g, t or u
```

```
<220> FEATURE:
<221> NAME/KEY: misc_feature
<222> LOCATION: (274)..(274)
<223> OTHER INFORMATION: n is a, c, g, t or u
<220> FEATURE:
<221> NAME/KEY: misc_feature
<222> LOCATION: (276)..(276)
<223> OTHER INFORMATION: n is a, c, g, t or u
<220> FEATURE:
<221> NAME/KEY: misc_feature
<222> LOCATION: (280)..(280)
<223> OTHER INFORMATION: n is a, c, g, t or u
<220> FEATURE:
<221> NAME/KEY: misc_feature
<222> LOCATION: (283)..(285)
<223> OTHER INFORMATION: n is a, c, g, t or u
<220> FEATURE:
<221> NAME/KEY: misc_feature
<222> LOCATION: (287)..(288)
<223> OTHER INFORMATION: n is a, c, g, t or u
<220> FEATURE:
<221> NAME/KEY: misc_feature
<222> LOCATION: (294)..(294)
<223> OTHER INFORMATION: n is a, c, g, t or u
<220> FEATURE:
<221> NAME/KEY: misc_feature
<222> LOCATION: (302)..(303)
<223> OTHER INFORMATION: n is a, c, g, t or u
<220> FEATURE:
<221> NAME/KEY: misc_feature
<222> LOCATION: (305)..(305)
<223> OTHER INFORMATION: n is a, c, g, t or u
<220> FEATURE:
<221> NAME/KEY: misc_feature
<222> LOCATION: (307)..(308)
<223> OTHER INFORMATION: n is a, c, g, t or u
<220> FEATURE:
<221> NAME/KEY: misc_feature
<222> LOCATION: (310)..(310)
<223> OTHER INFORMATION: n is a, c, g, t or u
<220> FEATURE:
<221> NAME/KEY: misc_feature
<222> LOCATION: (316)..(316)
<223> OTHER INFORMATION: n is a, c, g, t or u
<220> FEATURE:
<221> NAME/KEY: misc_feature
<222> LOCATION: (318)..(319)
<223> OTHER INFORMATION: n is a, c, g, t or u
<220> FEATURE:
<221> NAME/KEY: misc_feature
<222> LOCATION: (321)..(322)
<223> OTHER INFORMATION: n is a, c, g, t or u
<220> FEATURE:
<221> NAME/KEY: misc_feature
<222> LOCATION: (326)..(326)
<223> OTHER INFORMATION: n is a, c, g, t or u
<220> FEATURE:
<221> NAME/KEY: misc_feature
<222> LOCATION: (330)..(332)
<223> OTHER INFORMATION: n is a, c, g, t or u
<220> FEATURE:
<221> NAME/KEY: misc_feature
<222> LOCATION: (334)..(334)
<223> OTHER INFORMATION: n is a, c, g, t or u
<220> FEATURE:
<221> NAME/KEY: misc_feature
<222> LOCATION: (339)..(339)
<223> OTHER INFORMATION: n is a, c, g, t or u
<220> FEATURE:
<221> NAME/KEY: misc_feature
<222> LOCATION: (344)..(344)
<223> OTHER INFORMATION: n is a, c, g, t or u
<220> FEATURE:
<221> NAME/KEY: misc_feature
<222> LOCATION: (346)..(346)
<223> OTHER INFORMATION: n is a, c, g, t or u
<220> FEATURE:
<221> NAME/KEY: misc_feature
<222> LOCATION: (350)..(350)
```

```
<223> OTHER INFORMATION: n is a, c, g, t or u
<220> FEATURE:
<221> NAME/KEY: misc_feature
<222> LOCATION: (355)..(355)
<223> OTHER INFORMATION: n is a, c, g, t or u
<220> FEATURE:
<221> NAME/KEY: misc_feature
<222> LOCATION: (358)..(359)
<223> OTHER INFORMATION: n is a, c, g, t or u

<400> SEQUENCE: 55
nnnnnnnnnn nannnnnnnn ntatgcatta atgggttata attcactgaa aaatagtaac      60
gtacttctta actttggctt tcagagttcg aaccaacgtg gcctcaacca gatttggaat     120
gtcaaaaagc agagtgtcta tttgatgaat ttgaggaaat ctggaacttt gggcnnngan     180
nttctnnngt ccgggcgncc nnntctccnc ccngnctcnc tgcatncntg gagacccagt     240
cnccntcccc gtnctgnnnc ngnngcatna ngantnggcn ccnnntnntt tttnagccgg     300
anncngnntn tcaccngnnc nngccngcan nncnttgcnt cttntntgtn cagcngtnn      359

<210> SEQ ID NO 56
<211> LENGTH: 153
<212> TYPE: DNA
<213> ORGANISM: Artificial sequence
<220> FEATURE:
<223> OTHER INFORMATION: Synthetic oligonucleotide

<400> SEQUENCE: 56
tatgcattaa tgggttataa ttcactgaaa aatagtaacg tacttcttaa ctttggcttt      60
cagagttcga accaacgtgg cctcaaccag atttggaatg tcaaaaagca gagtgtctat     120
ttgatgaatt tgaggaaatc tggaactttg ggc                                  153
```